United States Patent [19]

Hillman et al.

[11] Patent Number: 5,383,848
[45] Date of Patent: Jan. 24, 1995

[54] IONTOPHORETIC ADMINISTRATION OF DRUGS

[75] Inventors: Robert S. Hillman; John M. Pawelchak, both of San Diego, Calif.

[73] Assignee: Gensia, Inc., San Diego, Calif.

[21] Appl. No.: 680,577

[22] Filed: Apr. 4, 1991

Related U.S. Application Data

[63] Continuation-in-part of Ser. No. 509,332, Apr. 12, 1990, abandoned.

[51] Int. Cl.$^6$ ............................................. A61N 1/30
[52] U.S. Cl. ........................................ 604/20; 128/898
[58] Field of Search ............... 128/798, 802, 803, 898; 604/20; 607/149-153

[56] References Cited

U.S. PATENT DOCUMENTS

| | | | |
|---|---|---|---|
| 4,722,726 | 2/1985 | Sanderson et al. | 604/20 |
| 4,845,233 | 7/1989 | Higuchi et al. | 548/320 |
| 5,023,085 | 6/1991 | Francoeur et al. | 604/20 |
| 5,088,977 | 2/1992 | Sibalis | 604/20 |
| 5,135,480 | 8/1992 | Bannon et al. | 604/20 |

Primary Examiner—John D. Yasko
Assistant Examiner—Michael Rafa
Attorney, Agent, or Firm—Lyon & Lyon

[57] ABSTRACT

Methods, formulations, and a system for improved iontophoretic administration of a drug, by, preferably, topical administration of a formulation containing an active vasodilator, rubefacient, or counterirritant agent such as capsaicin on the skin at the electrode site, or, iontophoretic administration of a vasodilator formulation or alpha blocker prior to iontophoretic administration of the drug.

8 Claims, 16 Drawing Sheets

IONTOPHORETIC ADMINISTRATION OF DRUGS

CROSS REFERENCE TO RELATED APPLICATIONS

This application is a continuation-in-part of U. S. Ser. No. 509,322 filed Apr. 12, 1990, for "Improved Iontophoretic Administration of Drugs", the disclosure of which is incorporated herein by reference.

FIELD OF THE INVENTION

The present invention is directed to increasing dermal clearance of transdermally administered drugs. In one aspect, the invention relates generally to improved methods, formulations and an improved system for iontophoretically administering drugs. These improvements are effective to reduce the time required to clear drugs believed to collect in a depot, or region beneath the surface of the skin underlying the electrode used for the iontophoretic administration of the drug. The formulations useful in the present invention are referred to as dermal clearance enhancers.

BACKGROUND OF THE INVENTION

Iontophoresis is the transport of ionized or charged species by application of an electrical current. Transdermal iontophoresis is the transport of an ionic drug through the skin of a mammal, usually a human, by passing a current through a drug-containing electrode placed against the skin. A second electrode, termed the return or indifferent electrode, is placed against the skin, normally several inches from the first. The current is evoked by applying a potential between the electrodes in a constant DC, pulsed DC or AC mode. The current carries the ionized drug "through" the stratum corneum into the dermis where the drug diffuses into the capillaries situated near the dermalepidermal junction, and then into the systemic circulation.

During clinical trials and animal experiments of drugs which increase heart rate and are therefore effective as exercise simulating agents, it was observed that after transdermal iontophoretic administration of the drug the time required to return the elevated heart rate to or near the normal, or baseline heart rate was not as fast as desired.

Although the present invention has general application in virtually all circumstances where a drug is administered iontophoretically, the primary intended uses are in conjunction with administration of certain exercise simulating agent (ESA TM) drugs on human patients, as described in several commonly assigned and co-pending patent applications. For this reason additional background will be provided concerning these exercise simulating agent drugs and the delivery systems, including the electrodes, preferably used.

Exercise simulating agents are drugs that elicit acute and adaptive cardiovascular responses similar to the types of responses elicited by aerobic activity. They are particularly useful, therefore, as a substitute for exercise stress testing for diagnosing cardiovascular diseases, due to their ability to increase heart rate, myocardial contractility, arterial blood pressure, and coronary and skeletal muscle blood flow. Exercise simulating agents of sufficient potency and iontophoretic mobility can be advantageously delivered, i.e., transported through the stratum corneum, using iontophoresis.

The amount of drug transported into the skin per unit time per unit area is known as the flux. Flux is proportional to the applied electrical potential and the drug concentration on the outside of the skin. The upper limit of current density to ensure that the current will not damage the skin is generally considered to be 0.5 mAmp/cm$^2$ of DC current. Other limits on flux include drug solubility, the partition coefficient of drug in the stratum corneum, and the drug's iontophoretic mobility. Clinically effective transdermal iontophoresis must be achieved within these limits on the flux.

In addition to the above-listed factors, the flux is greatly affected by several other factors. For example, the drug's ability to pass freely, i.e., its mobility often depends on the pH of the solution in which it is delivered, and optimum iontophoretic mobility requires that the drug be ionized or in charged form at some specific pH. Also, reduced iontophoretic efficiency, i.e., lower flux of a given drug, can result from the presence of other ionic species in the formulation. These other ions will "compete" with the drug ions as current carriers and can drastically reduce iontophoretic flux.

Known problems associated with iontophoretic delivery of drugs include electrical or chemical burns, dermal irritation, incompatibility between the drug and other excipients in the drug-containing medium, slow onset of pharmacologic activity and lack of drug delivery response to application and removal of current, drug degradation due to anodic current flow, pH change, and unsatisfactory drug storage capability. The present invention addresses several of these problems in order to help achieve safer, more reliable and more convenient medical transdermal iontophoresis.

Regarding the specific electrodes useful in conjunction with the present invention three have been specifically proposed for transdermal iontophoresis, these being classified as: (1) monolithic pad; (2) reservoir pad; and (3) multilayer pad. All three may be used in conjunction with the present invention.

A monolithic electrode pad design provides for including the drug in a polymer or matrix that is attached to the electrode. The polymer may contain an adhesive to maintain contact with the patient's skin. The drug is dispersed in the polymer during manufacture and the polymer is then formed into the pad itself. An example of the class of polymers suitable for use in such pads are hydrogels, for example, poly(hydroxy ethyl methacrylate) (HEMA).

A reservoir electrode pad design allows for addition of the drug to an electrode which includes a disk and which is attached to the patient's skin. In such a design, the drug is contained in a reservoir or cavity formed during the manufacture of the electrode. The drug can be added in gel form during manufacture of the pad, after its manufacture, or immediately prior to use to form the drug-containing matrix.

A multilayer electrode pad includes separate layers for a buffering solution, an ion-exchange membrane and a drug reservoir.

Regardless of the design of the drug delivery electrode pad, the pad itself may be of any shape, but it should conform to the area of the body where it is applied. The size of the pad may be up to about 20 cm$^2$, but preferably is only as large as required to keep current density below 0.5 mAmp/cm$^2$. Although not fully understood, reduced current density may be a major factor in avoiding pH changes, damage to the patient's skin and build up of drug in a depot, or region in the dermis.

If the drug-containing matrix itself has no buffering capacity, the electrode material should include a material that undergoes an oxidation reduction reaction, such as silver/silver chloride, zinc/zinc chloride, or carbon-filled electrodes. It may be desirable to add a small amount of buffer, e,g., citrate or phosphate buffer, to maintain the desired pH in the electrode.

The gel may comprise a soluble polyHEMA, such as hydroxyethylmethacrylate available from Benz Research; hydroxypropylmethyl cellulose sold as Methocel TM, ElOM, by Dow Chemical or Carbopol available as 934P, from B. F. Goodrich, and may include a preservative to prevent microbial growth. Parabens, such as methyl, ethyl and propyl are preferred preservatives. Small amounts of EDTA as a chelating agent may be included. Preferred gels also include an antioxidant to prevent oxidation due to the drug-electrode interaction. Preferred antioxidants include sodium bisulfite and vitamin C. The solvent for the gel may comprise deionized, pyrogen-free water or polyethylene glycol, such as PEG 400, 10–20%. If desired, ethanol, 100%, may be added as a co-solvent. The concentration of the drug within the gel is preferably in the range of approximately 5–25 mg/ml.

Prior to placing the drug delivery electrode pad on the skin of the patient, it may be desirable for the technician or doctor to abrade the skin using a clinically acceptable tape material or other method. This removes part of the stratum corneum, the main barrier to transport of the drug into the dermis. Permeation enhancers may be applied topically prior to applying the drug delivery electrode pad to increase the flow of the drug through the stratum corneum. Preferred permeation enhancers include surfactants such as sodium lauryl sulfate.

As described in more detail in application Ser. No. 308,683, filed Feb. 9, 1989, the preferred system used for delivery of the ESA TM drug includes a conventional power source operatively connected to the subject, typically a human, and having the capability to control or regulate the rate at which the drug is administered. The system also includes a conventional electrocardiographic monitoring device connected to the subject and a conventional microprocessor operatively connected to both the power source and the electrocardiographic monitoring device so that heart rate, changes in heart rate and drug delivery may be monitored, displayed and controlled or regulated.

Consistent with the above background and for the purpose of more fully understanding the primary expected uses of the present invention, several commonly assigned and co-pending applications directed to specific ESA" drugs and systems are incorporated herein by reference. These applications are listed as follows:

U.S. patent application Ser. No. 308,683, filed Feb. 9, 1989, is directed to the diagnosis, evaluation and treatment of coronary artery disease by exercise simulation using a closed loop drug delivery of an exercise simulating agent beta agonist by iontophoresis;

U.S. patent application Ser. No. 471,296, filed Jan. 26, 1990, is directed to an apparatus and method for iontophoretic transfer of drugs; and U.S. patent application Ser. No. 471,178, filed Jan. 26, 1990, is directed to an iontophoretic transfer electrode and a method of transdermal drug delivery.

All of these applications are directed to iontophoretic delivery of certain drugs known as exercise simulating agent beta agonists (hereinafter referred to as "exercise stimulating agents", ESA" Beta Agonists or ESA" drugs).

Reference is also made herein to other publications. All such publications referred to herein are incorporated by reference and are listed in the Bibliography which immediately precedes the claims.

SUMMARY OF THE INVENTION

The term "dermal clearance enhancer" refers to an agent which increases or enhances the dermal clearance of a therapeutic agent or drug, i.e., the rate at which the drug moves through or is "cleared" from skin tissue. Parameters indicative of the rate of dermal clearance include flux of the drug or, if the drug has a measurable physiological response, offset of the response after drug administration is discontinued. When a drug is administered transdermally, especially by transdermal iontophoresis, a "depot" of the drug may build up in the skin, such that when administration of the drug is discontinued, there is a delay in decrease in drug levels and thus in "offset" of the drug effect. For example, in the iontophoretic administration of a drug which increases heart rate, there may be a delay in return to the baseline heart rate following discontinuation of iontophoretic administration. These dermal clearance enhancers ("DCE") increase clearance of drug from skin and thus decrease the offset time and the time for heart rate to return to base line levels.

The present invention is directed to methods and formulations for enhancing dermal clearance of transdermally administered drugs. These dermal clearance enhancers are particularly useful in enhancing clearance of drugs administered by transdermal iontophoresis. In one aspect of the present invention, these DCE formulations are administered as a pretreatment, prior to transdermal iontophoretic administration of the drug whose dermal clearance is to be enhanced. Preferably, the DCE formulations comprise an agent which produces vasodilation. Such vasodilation may be produced by specific vasodilators, counterirritants or rubifacients. In one preferred embodiment, the suitable DCE formulations are those which may be administered topically; alternatively DCE formulations which are administered iontophoretically may be used. Preferred DCE formulations include those which comprise an agent which when administered topically produces vasodilation.

During transdermal iontophoretic administration of drugs, especially exercise simulation beta agonist drugs, it is believed that a depot of drug accumulates in and/or near the dermis and that this accumulation prevents a rapid decline in heart rate after the current is turned off. In accordance with the present invention certain formulations are used as pretreatment agents for the purpose of producing dilation of the blood vessels near the site where the drug is administered. Preferred formulations are administered topically and include one or more active agents which function to dilate the blood vessels. These preferred formulations are administered prior to administration of the drug to enable sufficient dilation of the blood vessels, with the preferred pre-treatment time being about 10 minutes prior to the start of iontophoretic drug delivery.

Alternate formulations may be administered by iontophoresis prior to iontophoretic administration of the drug itself. Some formulations may be administered topically as well as iontophoretically.

In one aspect, the formulations and methods of the present invention are preferably used in a system which includes apparatus for administering the drug and pretreatment formulation, apparatus for monitoring the amount of drug delivered and the heart rate of the subject, and apparatus for controlling the rate of drug administration in response to heart rate.

OBJECTS OF THE INVENTION

Figure 1:
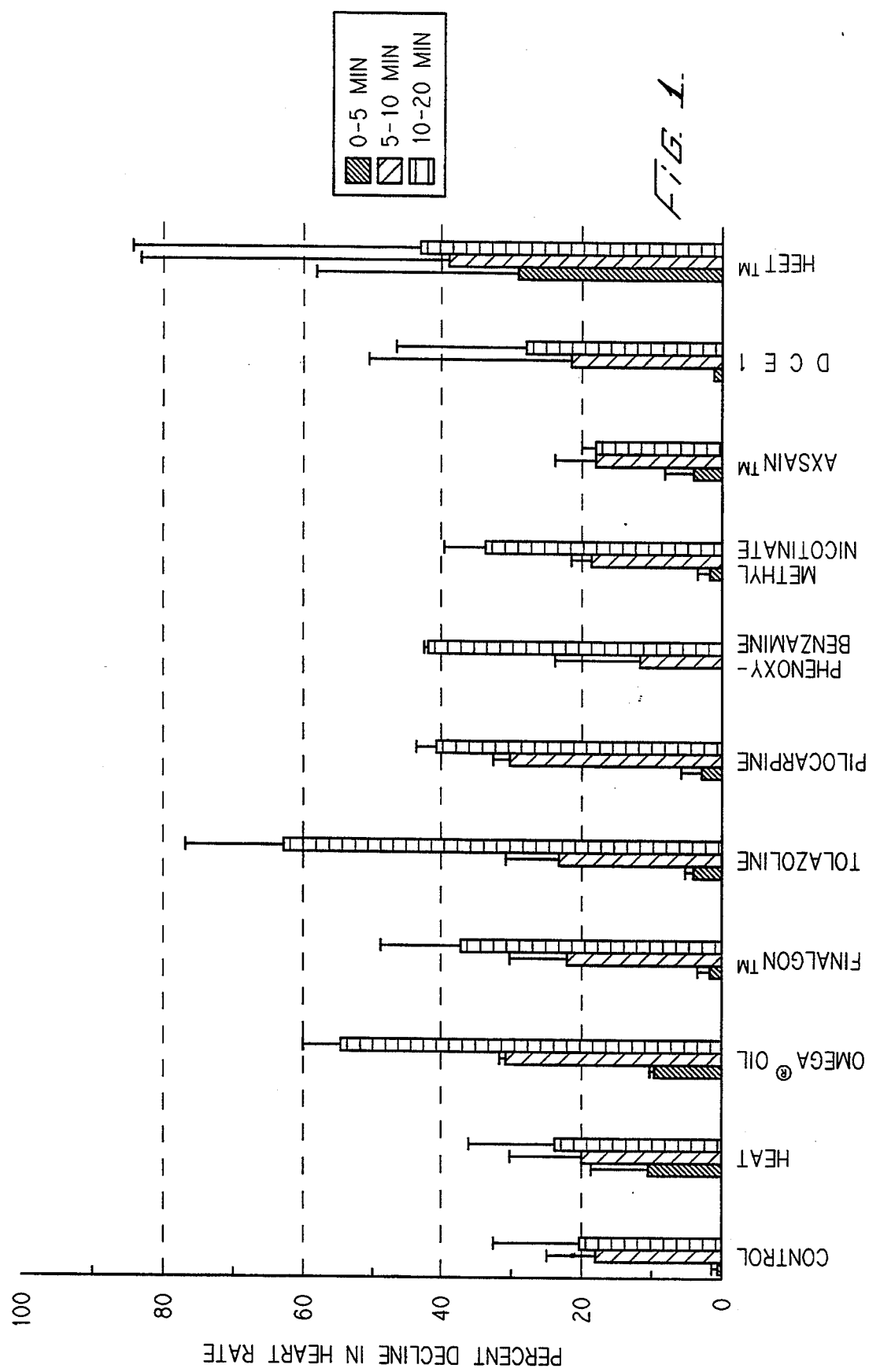
FIG. 1 is a bar graph illustrating the relative percent decline in elevated heart rate associated with application of various vasodilator formulations of the present invention compared to a control.

It is an object of the purposes of the present invention to safely and effectively minimize the offset associated with transdermal iontophoresis.

It is a further object of the present invention to provide a method of enhancing clearance of iontophoretically administered drug from the dermis.

It is a further of object of the present invention to provide formulations which, when administered to the skin will function to enhance clearance of iontophoretically administered drug found in and/or near the dermis.

It is a further object of the present invention to provide a system which is capable of iontophoretic administration of a drug and of enhancing clearance of the drug from and/or near the dermis.

It is a further object of the present invention to provide methods, formulations and a system which may be used to iontophoretically administer an exercise simulation drug to a mammal and to minimize the time delay between when transport of the drug through the skin is stopped and the mammal's elevated heart rate begins to decline.

It is a further object of the present invention to provide an alcohol-based formulation and a method of topical pretreatment to minimize the time delay associated with iontophoretic administration of exercise simulation beta agonist drugs to humans by enhancing clearance of the drug from a depot in the dermis.

It is a further object of the present invention to provide a more rapid response to a patient's request for medication in patient controlled analgesia environments.

DETAILED DESCRIPTION OF THE INVENTION

In accordance with the background and objectives of the invention, and with reference to the Tables and Figures, preferred methods of reducing the depot effect are described below.

Preferred Dermal Clearance Enhancer Formulations

Preferably, the dermal clearance enhancer formulations of the present invention comprise an agent which produces vasodilation, wherein vasodilation is produced by specific vasodilators, counterirritants or rubifacients.

Preferred dermal clearance enhancer formulations of the present invention include formulations suitable for being topically administered. In one preferred aspect, these formulations are administered topically as a pretreatment prior to administration of a drug by transdermal iontophoresis. We have found pretreatment times on the order of about 10 minutes to be suitable.

Preferred DCE formulations comprise an agent which when administered topically produces vasodilation. Suitable vasodilators include esters of nicotinic acid, especially lower alkyl or benzyl esters; products derived from peppers of the family Solanaceae such as capsicum, capsicum oleoresin, capsaicin, and nonivamide; methylsalicylate, histamine, camphor and the like. For ease of administration, commercially available rubefacient, topical vasodilator and counter irritant formulations may be used. Some of such formulations are described infra herein.

Preferred are DCE formulations for topical administration comprising one or more of the following:
(a) from about 0.1 to about 5% of an ester of nicotinic acid; preferred esters include methyl, butyl and benzyl;
(b) from about 0.01 to about 5%, preferably from about 0.02% to about 0.3% capsaicin;

(c) from about 0.01 to about 5%, preferably from about 0.02% to about 0.3% nonivamide;

(d) from about 0.1 to about 5%, preferably from about 0.2% to about 3% capsium or capsium oleoresin;

(e) from about 5% to about 30%, preferably from about 15% to about 20% methyl salicylate;

(f) from about 0.01% to about 5% histamine; and (g) from about 2% to about 20%, preferably from about 3% to about 10% camphor.

Preferred DCE formulations for iontophoretic administration comprise an agent which produces vasodilation, preferably, a vasodilator selected from about 0.2% to about 5% tolazaline, from about 0.2% to about 5% phentolamine, from about 0.05% to about 2% phenoxybenzamine, and from about 0.01% to about 1% pilocarpine.

Preferred vehicles for the DCE formulations of the present invention comprise a mixture of a short chain aliphatic alcohol, such as ethanol or isopropanol, either light mineral oil or propylene glycol and methyl salicylate. Preferred ratios include about 2 to about 6 parts alcohol and from about 1 to about 4 parts mineral oil or propylene glycol per part methyl salicylate.

Description Of Preferred Embodiments Of The Invention

Based on results obtained in clinical trials and animal experiments, it was observed that after transdermal, administration of ESA TM drug the decline in heart rate from an elevated rate, i.e., its offset, was not as fast as desired for some applications. A relatively fast decline in offset is desired for the purpose of conducting diagnostic testing in a reasonable time and for the purpose of resolving signs of ischemia, if any are detected, as quickly as possible after ESA TM drug administration is stopped.

In accordance with the present invention it is presently believed that during transdermal delivery a depot of drug accumulates in and/or near the dermis after passage through the stratum corneum but prior to absorption in the capillaries located in and/or near the dermis. It is thus believed that this depot of drug results in a sustained drug delivery to the circulation after electrode current is stopped and that it therefore prevents a rapid decline in heart rate even after the current is turned off.

It is presently believed that the depot is a localized region, or volume, within and/or near the dermis. We refer to this phenomenon as the depot effect and refer to the localized volume in which the drug concentration resides as the depot.

Ideally, cessation of transport of the drug through the stratum corneum would result in cessation of transport of drug into the bloodstream. However, because of the depot effect, a delay exists between the time when drug transport from the electrodes is stopped and when no more drug enters the blood-stream from the depot in the dermis. Thus, after cessation of drug transport at the end of diagnostic testing, or for any other reason, the drug remaining in and/or near the dermis continues to be transported into the bloodstream and continues to maintain the heart rate an elevated level. Consistent with one of the objectives of the present invention the preferred embodiments minimize this time delay and, in particular, minimize the time delay associated with iontophoretic administration of ESA TM Beta Agonist drugs by enhancing clearance of the drug from the depot. The time required to return elevated heart rate to normal is referred to as "offset time" or simply as the "offset." Alternatively, within the scope at the present invention the term offset may be used to refer to the time required to clear a drug from the skin or the time required to reduce the concentration of a drug in the skin to some given, lower concentration after iontophoretic administration of the drug.

The depot effect is believed to be an example of dermal clearance limited by the state of local vasomobility or perfusion rate as discussed in Tregear (1966), Barry (1983) and Riviere, et al. (1988). In circumstances wherein the iontophoretic flux of drug into the skin exceeds the removal rate by the underlying vasculature, it is believed that the drug may accumulate in the adjacent tissue to form a drug depot. Support for existence of such a situation may be derived from theoretical concepts such as those set forth in Norman (1975).

Conditions sufficient for depot formation for a highly water-soluble ionic drug such as ESA TM Beta Agonist are believed to arise when (a) the capillary area for tissue-to-capillary transfer is transport-rate limiting; (b) the rate of blood flow, i.e., perfusion rate, becomes transport-rate limiting; (c) a state of vasoconstriction, induced by the drug itself, becomes transport-rate limiting as described in Barry (1983); and/or (d) transport-rate limitation is related to capillary permeability.

The physico-chemical nature of a transport-rate-limited depot differs from that involving a reservoir effect due to drug partitioning in the stratum corneum. This latter type of depot has been implicated in some cases of passive transdermal drug delivery, as discussed in Tojo (1988), but this type of depot is not likely to be present during administration of the preferred ESA TM drugs, particularly since the partitioning of ionic moieties in the stratum corneum is not favored. In this context, the term "partitioning" is used to refer to the phenomenon whereby higher drug concentration may be achieved in this region compared to other regions, such as in the drug-containing matrix in the electrode, as is commonly understood by those skilled in the art.

It also recognized that dermal clearances may be delayed by drug tissue binding in the skin as that term is understood by those skilled in the art. However, transport to the systemic circulation would not necessarily be increased by vasodilator effects on the absorbing vasculature in this instance since the magnitude of the tissue binding constants is independent of the state of vasodilation in the region. Also, as will be shown in greater detail, alterations in the depot effect associated with the ESA TM drug may be induced by vasodilation elicited by both specific adrenergic blocking agents or nonspecific counterirritants or rubefacients applied in various manners. This indicates that even if tissue binding is occurring it does not necessarily significantly compromise dermal clearance enhancement as described in this invention.

In accordance with the objects of the invention, it has been discovered that the depot effect preferably may be reduced by the use of topically administered vasodilatory agents. These agents are believed to principally function to increase the dermal clearance of the drug by modifying the underlying transport-rate -limiting conditions associated with the vasculature in the skin. This beneficial function results from vasodilation of the capillaries evoked by topically applied agents that are commonly used and categorized as topical vasodilators, counterirritants or rubefacients. Agents classified as such have been described as causing a spectrum of effects on the vasculature. These include vasodilation in addition to increases in capillary permeability, as recognized in Goodman and Gillman (1980).

As useful alternate embodiments of the present invention, it has been discovered that certain vasodilators and/or alpha blockers function to increase the rate of dermal clearance when iontophoretically pre-administered. However this method is not the preferred one, for reasons set forth below.

The present invention may also be used in administration of patient controlled analgesics such as opioids. In drug administration environments where the patient may control the delivery of analgesics, various drugs, such as Fentanyl ™ may be delivered iontophoretically. For any such analgesic which forms a drug depot in the dermis, drug would continue to be released after an initial transdermal delivery. In patient controlled analgesia (PCA), the problem could be exacerbated by the patient pushing the administration button and receiving a bolus of analgesic multiple times, which action could result in formation of an enlarged depot that could last for a relatively long time. In extreme cases the patient may become over-medicated and this condition could lead to serious side effects, e.g., respiratory difficulties. Therefore, another object of the present invention is to provide a more rapid response to a patient's request for medication in PCA environments, with the attendant reduction in risk of over-medication.

The methods of the present invention comprise application of vasodilator formulations prior to iontophoretic administration of an ESA™ drug, i.e., a pretreatment. The formulations whether novel or conventional, function as dermal clearance enhancers and are advantageous because they aid in reducing the offset time. For purposes of the present invention, the term vasodilator refers to and includes any pharmacologic or environmental agent which produces dilation of the blood vessels through either systemic or topical application. In accordance with the present invention the vasodilator formulation may be applied by non-invasive techniques such as through pre-delivery iontophoretically or especially by topical pre-application of a vasodilator formulation to the skin at the electrode site. The pre-application of an alcohol-based topical vasodilator solution is the most preferred method.

In addition to reducing the offset, another advantageous feature of the dermal clearance enhancers of the present invention is their potential to reduce risk of skin irritation related to the existence of a drug depot in the dermis. Also, the methods and formulations of the present invention have been found to permit repeated administration of drug, thus making them additionally advantageous especially in PCA applications.

The topically applied formulations share an additional advantage in that they may be administered by simple, direct application to the skin, and are therefore easier to use than the iontophoretically administered dermal clearance enhancers.

For purposes of the present invention the terms vasodilation and vasodilator are used to refer to and include the phenomenon of increased blood flow in the dermis, and, any compound which functions to increase blood flow in the dermis, respectively.

This increase in blood flow in the dermis may be achieved by specific, i.e., pharmacologic, or nonspecific activity. An example of the first class of agents would be histamine. Examples of the latter class of agents are the counterirritant/rubefacient agents such as capsicum or its components or the esters of nicotinic acid. As noted in Drill (1971), these agents, also known as local irritants, may produce a spectrum of responses from vasodilation through rubefacience largely as a function of the concentration applied. Further, an increase in vasodilation may be accompanied by capillary permeability increases, as recognized in Goodman and Gillman, 1980.

The most preferred vasodilator formulations contain topical vasodilator agents commonly known as rubefacients or counterirritants. The phenomenon of rubefacience is generally understood to be caused by vasodilation. Rubefacient agents are primarily the nicotinates including methyl, ethyl, butoxyethyl, phenethyl and thurfyl as well as the essential oils such as mustard, turpentine, cajuput and capsicum, as listed in Barry (1983).

The most preferred topical vasodilator formulations of the present invention include active vasodilator agent(s) in an alcohol or hydroalcoholic vehicle. The vehicle may also contain other pharmaceutically acceptable ingredients such as mineral oil or propylene glycol which function to provide additional solvent properties, to produce cosmetic acceptability or to provide occlusion.

Active Vasodilator/Counterirritant/Rubefacient Agents

The most preferred active vasodilator/counterirritant/ rubefacient agents of the present invention include a component of capsicum and/or the methyl ester of nicotinic acid and/or nonivamide.

Capsicum is the dried ripe fruit of *Capsicum frutescens* Linné, or of *Capsicum annuum Linne, Var. conoides Irish*, or of *Capsicum Annuum Var. longum* Sendt, or of a hybrid between the Honka variety of Japanese Capsicum and the Old Louisiana Sport Capsicum known in commerce as Louisiana Sport Pepper (Fam. Solanace ). See, The *United States Pharmacopeia*, Twenty-First Revision, Official from Jan. 1, 1985—*The National Formulary*, Sixteenth Edition, Official from Jan. 1, 1985, pages 72–73. See also Leung.

Although it is presently believed that any compound falling within the above definition of vasodilator and approved for use on the human skin will provide enhanced reduction of the offset associated with iontophoretic administration of drugs, one most preferred active ingredient is capsaicin, which is one of several known components of capsicum. This preferred rubefacient active ingredient is also known as capsacin, the British spelling of capsaicin. The structural formula of capsaicin is:

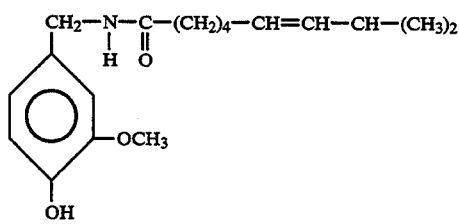

In preferred rubefacient formulations, capsaicin is present in the amount of about 0.01% to about 1% by weight, with a presence of about 0.025% by weight believed to be optimum.

In the oleoresin form, about 0.1% to about 0.5% by weight is preferred and about 0.25% is believed to be optimum. Referring to the Tables and Figures, it has also been discovered that the methyl ester of nicotinic acid significantly improves the rate of dermal clearance of ESA ™ drug depot and is also therefore a preferred agent within the scope of the present invention. Although methyl nicotinate is a well known topical vasodilator, as discussed in, for example, Tur (1983), Guy (1982) and Collins (1984), its ability to cooperate with iontophoretically administered ESA ™ drugs so as to result in reduction of the associated offset has not heretofore been known or suggested.

Also, preferred active ingredients may include those compounds having chemical structure and properties similar to that of capsaicin, such as, for example, nonivamide, or, as it is sometimes referred to, capsicine Nonivamide is N-vanillylnonamide, $C_{17}H_{27}NO_3$, having the structural formula:

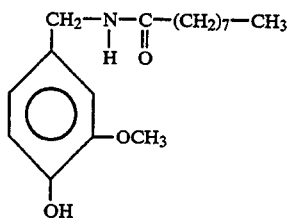

Nonivamide may be used in preferred concentrations of about 0.4% by weight as an active rubefacient agent in the present invention, and is believed to be effective in amounts of 0.1–0.5% by weight. Commercially available formulations containing nonivamide are sold under the name Finalgon ®, Rheumaplast ™ and Rubriment ™.

Although preferred compounds effective within the present invention are generally known as topical vasodilators and counterirritants, other, and conflicting nomenclature and definitions are known to describe these compounds. For example, some of the compounds listed in the Federal Register, Vol. 48, No. 27, Tuesday, Feb. 8, 1988, regarding proposed Rule §348.12 Counterirritant active ingredients, at page 5868 are believed to be effective agents, singly or in combination, within the scope of the present invention even though some are not explicitly listed therein as producing vasodilation. These compounds and the concentrations are as follows:

1. Allyl isothiocyanate, 0.5 to 5.0 percent.
2. Methyl salicylate; 10 to 60 percent.
3. Turpentine oil, 6 to 50 percent.
4. Histamine dihydrochloride, 0.025 to 0.10 percent.
5. Methyl nicotinate, 0.25 to 1.00 percent.
6. Capsaicin, 0.025 to 0.25 percent.
7. Capsicum (about 10% active ingredients) in an amount to contain about 0.025 to 0.25 percent capsaicin.
8. Capsicum oleoresin (about 10% active ingredients) in an amount to contain about 0.025 to 0.25 percent capsaicin. See also Federal Register, Vol. 44, No. 234, pages 69804–05.

In addition to the active ingredient(s), the most preferred rubefacient formulations also include an alcohol carrier, water, mineral oil and/or other pharmaceutically acceptable solvents or ingredients such as propylene glycol and/or water. For example, cetyl alcohol may be used to impart well known cosmetic effects.

A. Alcohol Vehicle

In the preferred rubefacient formulations alcohol is present in the amount of approximately 25% to about 75% by weight. The most preferred of the rubefacient formulations include an alcohol in about 50% by weight.

Although the function of the alcohol is not fully understood, it is presently believed that the alcohol functions to maximize the penetration of the active ingredient(s) into the dermis, i.e., to maximize the depth and speed of penetration of the active ingredient(s) in the formulation into the dermis.

In general, the preferred alcohols are U.S.P./N.F. grade alcohols approved for application to human skin. For example, isopropyl alcohol is the most preferred alcohol, although others such as ethyl alcohol and butyl alcohol are also preferred. All of these alcohols are available as U.S.P./N.F. grade alcohols approved for application to human skin. Also, other alcohols approved for application to human skin such as propylene glycol are considered to be equivalent alcohols within the scope of the present invention, even though not specifically listed herein. Furthermore, other alcohols not necessarily approved for application to human skin are considered to be equivalent for purposes of the present invention for use in animal testing and for other uses not requiring application to the human skin.

B. Mineral Oil

In the preferred formulations of the present invention, mineral oil from approximately 10% to approximately 50% by weight is used, with about 30% by weight mineral oil believed to be optimum. Although the function of the mineral oil in the preferred formulations is not fully understood, it is presently believed that the mineral oil may function in part to reduce or prevent alcohol evaporation from the skin, and thus act as an occlusive agent with respect to the alcohol.

The preferred mineral oils of the present invention are U.S.P./N.F. mineral oils commercially available and approved for application to human skin. All such mineral oils are equivalent for purposes of the present invention when used for application on humans. For other applications, other mineral oils are considered to be equivalent for purposes of the present invention.

C. Commercially Available Rubefacient Formulations

There are presently a number of commercially available alcohol-based formulations that may be used in the present invention. Such formulations are sold commercially as OMEGA ® Oil and Heet ™.

Rubriment ™ is manufactured by Nordmark, is available in Germany and contains benzyl nicotinate, 2.0%; salicylamide, 0.2%; hydroxyethyl salicylate, 1.8%; camphor, 3.0%; nonivamide, 0.1%; and turpentine oil, 3.0% in an emulsion vehicle. Also available in the U.S. is a formulation sold as Heet ™ Spray, which contains 25% methyl salicylate, 3.0% menthol, 3.0% camphor and 1.0% methyl nicotinate in an isopropyl alcohol vehicle.

Novel Topical Vasodilator Formulations of the Present Invention

In accordance with the present invention several novel formulations containing one or more active vasodilation agents have been prepared. Some of these has been used in the in vivo testing reported in Tables I–VII and described supra. These formulation are known as Dermal Clearance Enhancer 1 (DCE 1) to 6 and contains the following ingredients as noted below. These novel formulations have been prepared, and based on a set of experiments on human volunteers to determine the existence and degree of vasodilation/irritation, are considered to be preferred vasodilator formulations within the scope of the present invention. These additional novel formulations and their ingredients are listed below:

| Identity | Ingredients |
| --- | --- |
| DCE-1 | Methyl nicotinate, 0.27% and capsaicin, 0.24% in 50/50 (v/v) isopropyl alcohol to water. |
| DCE 2 | Histamine dihydrochloride, 0.02% in a 50/50 (v/v) isopropyl alcohol to water vehicle. |
| DCE 3 | Capsaicin, 0.24% in 70% ethyl alcohol. |
| DCE 4 | Capsicine (nonivimide), 0.24% in 70% ethyl alcohol. |
| DCE 5 | Methyl nicotinate, 0.24% in 70% ethyl alcohol. |
| DCE 6 | Capsaicin, 0.075% and Methyl nicotinate, 0.25% in 50/50 (v/v) isopropyl alcohol to water. |

Other preferred novel DCE compositions include the formulations listed below. Some of these formulations have also been used in in vivo testing as reported in Table VII and FIGS. 8 and 13 and described supra. These formulations and their ingredients are listed below:

| Identity | Ingredients |
| --- | --- |
| Alpha oil | 0.27% (w/w) Methyl nicotinate, 0.24% capsicum oleoresin, 0.02% Histamine in a vehicle of 2.9:2.0:1.0 isopropylalcohol: light mineral oil:methylsalicylate |
| Beta oil | 0.27% (w/w) Methyl nicotinate, 0.028% Capsaicin, 0.02% Histamine dihydrochloride in a vehicle of 2.9:2.0:1.0 isppropyl alcohol:light mineral oil:methyl salicylate |
| Gamma Oil | 0.27% (w/w) Methyl nicotinate, 0.028% Capsaicin in a vehicle of 2.9:2.0:1.0 isopropyl alcohol:light mineral oil: methyl salicylate |
| Delta Oil | 0.27% (w/w) Methyl nicotinate, 0.028% Capsaicin in a vehicle of 2.9:2:1 ethyl alcohol: propylene glycol:methyl salicylate |

Cream-Based Topical Vasodilators

It has also been discovered that cream-based rubefacients will provide some improvement in reduction of the offset as described above. However, in general, the cream-based rubefacients are not as preferred as the alcohol-based rubefacients because they have been found not to reduce the offset time as quickly as or to the extent that alcohol-based formulations do.

One commercially available cream, or ointment-based formulation, sold under the name Axsain TM contains capsaicin, 0.075% in a washable ointment base, does, however, produce fairly good reduction in offset.

Another commercially available cream-based rubefacient useful in the present invention is marketed under the name Finalgon ® in the United Kingdom and West Germany. The entry in Martindale The Extra Pharmacopoeia for Finalgon ® cream is: "Finalgon (Boehringer Ingelheim, U.K.). Ointment containing butoxyethyl nicotinate 2.5% and nonivamide 0.4% ...." Other cream-based preparations containing nicontinates, histamine, capsicum component(s) and/or nonivamide and those listed on page 1626 of Martindale's are expected to be topical vasodilator formulations useful in the present invention, although not as preferred as the alcohol based formulations.

Specific Adrenergic Blocking Agents

It has been discovered that certain adrenergic blocking agents, i.e., alpha blockers which cause vasodilation, such as tolazoline, phentolamine and phenoxybenzamine, will function to reduce offset. Although the mechanism by which the alpha blockers operate in the context of the present invention not fully understood, it is believed that some alpha blockers perform a vasodilation function sufficient to be useful to reduce offset for the purposes of the present invention. These alpha blockers have been found effective when pre-delivered iontophoretically. It has been found that topical pre-treatment with tolazoline produces no measurable dermal clearance enhancement.

Topical Application of Topical Vasodilator Formulations

Certain vasodilator formulations of the present invention are useful in iontophoretic administration of drugs to humans and to animals when topically applied to the skin prior to iontophoretic administration of the drug. Although the time between application of the formulation to the skin and the beginning of iontophoretic administration of drug may vary according to individual subject, formulation type and strength, it has been discovered that approximately a ten minute interval is sufficient for most formulations and most people to ensure and optimize penetration of the active agent(s) and the duration of the effect. It has been discovered that topical application as short as five minutes and as long as two hours prior to administration of the ESA TM drug will enable excellent dermal clearance enhancement.

It is also believed that optimizing the pre-treatment time prior to the initiation of iontophoresis may include adjustment of the formulation strength of the dermal clearance enhancers. Also, the concentration of the formulation may be adjusted to help optimize the duration of dermal clearance enhancement for the therapeutic or diagnostic procedure intended.

In general, sufficient formulation should be applied to the skin to cover the active surface area of the electrode used to iontophoretically apply the drug. Also, for most rubefacient formulations, it has been discovered that the visually observable reddening of the skin after application of the formulation will mark the beginning of the time during which iontophoretic application of drug within the scope of the present invention may begin. Typically, this reddening phenomenon occurs approximately 7 to 10, minutes after application of the rubefacient formulation. It is emphasized, however, that not all vasodilators, especially those classified as counterirritants, cause reddening of the skin and thus such a phenomenon is not a reliable indicator in all cases.

It is believed that many rubefacients are also, but not necessarily, counterirritants and that many rubefacient formulations may, but not necessarily, include counterirritants. A counterirritant is an agent which produces a sensation upon application, usually topical, which "crowds out" the perception of pain in an underlying site. The perception of warmth or irritation, i.e., itching, often accompanies application of a counterirritant, but is not necessarily related to vasodilation. See also Drill (1971).

Application by Iontophoretic Pre-Delivery of Vasodilator

It has been discovered that by pre-delivering certain vasodilators iontophoretically prior to iontophoretic delivery of an ionic drug a significant reduction in the offset time may be achieved. For example, in this type of application of vasodilator, pre-administration of tolazoline was found to achieve a significant reduction in offset time when applied ten minutes prior to administration the ESA TM drug as shown in the various Tables and Figures herein. Additionally, it has been discovered that such pre-delivery of the vasodilators pilocarpine and methyl nicotinate as well as of the well known alpha blocker phenoxybenzamine also reduce offset time.

Due to lack of convenience resulting from use of two sets of electrode patches and because of possible regulatory concerns involved with iontophoretic delivery of two agents; however, this method is not as preferred as the topical pretreatment methods.

To assist in understanding the present invention, the following examples are included which describe the results of a series of experiments. These examples relating to the present invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

EXAMPLES

Example A

In Vivo Dog Experiments

In order to more clearly describe the present invention a series of in vivo experiments was conducted to compare the effect on the time delay, i.e., offset, in dogs due to the present invention methods of application and formulations compared to the offset associated with administration of the same drug to the same subjects, but without administration of dermal clearance enhancer.

These experiments were conducted on two labrador dogs, "BO" and "PO" having ages of approximately 2 years and weights of 32 and 20 kilograms, respectively.

In the following examples, the skin of the dogs was pretreated with a test formulation. In each data run, this pretreatment was followed by iontophoretic delivery of the ESA TM drug for ten minutes.

In each case the drug used to increase the heart rate was the ESA TM drug having the structural formula:

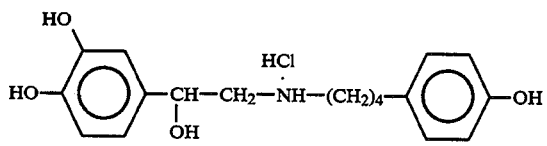

This compound is also identified as GP 2-121-3 in application Ser. No. 471,296 and has the chemical name 1-(3,4-dihydroxy-phenyl)-2-(4-(4-hydroxyphenyl)-butylamino)ethanol hydrochloride.

Ten pretreatments were administered to the two conscious dogs on different days. The same current profile and drug concentration was used in each data run, i.e., 2 mAmp for 7 minutes and 48mM (m Molar) of GP 2-121-3.

In the control runs a significant increase in heart rate resulted with no decline in heart rate during the first hour after administration of the ESA TM drug, and indicated the presence of a significant drug depot and associated offset.

Referring to Table I, 25 examples, or test data runs, identified according to dog and type of pretreatment are listed. The control runs are shown as Examples 1 and 2. In each case where a gel was used, the gel was a hydroxypropyl methylcellulose, sold as Methocel" preparation. The treatment types are summarized below:

1. Heat: A 3M gel heating pad was applied to the skin before, during and after drug administration at an approximate temperature of 60° C.
2. Tolazoline: Gel containing 0.1% of tolazoline was iontophoretically delivered at 0.6 mA for 10 minutes prior to drug administration.
3. Pilocarpine: Gel containing 0.05% pilocarpine was iontophoretically delivered at 0.6 mA for 10 minutes prior to drug administration.
4. Methyl Nicotinate: Gel containing 0.05% methyl nicotinate was iontophoretically delivered at 0.6 mA for 10 minutes prior to drug administration.
b 5. Phenoxybenzamine: Gel containing 0.1% phenoxybenzamine was iontophoretically delivered at 0.6 mA for 10 minutes prior to drug administration.
6. Omega ® Oil: A commercially available formulation sold as Omega ® Oil was topically applied 10 minutes prior to drug administration. Its active ingredients are: Methyl salicylate, 17.5%; histamine dihydrochloride, 0.02%; methyl ester of nicotinic acid, 0.27%; and capsicum oleoresin, 0.24% in a 50/50 (v/v) isopropyl alcohol to water vehicle.
7. Finalgon ®: A commercially available cream based formulation sold as Finalgon TM was topically applied 10 minutes prior to drug administration. Its active ingredients are: Butoxyethyl nicotinate, 2.5%; and nonivamide, 0.4%.
8. DCE 1: A novel formulation of the present invention was applied topically 10 minutes prior to drug administration. Its ingredients are: Capsaicin, 0.24%; methyl nicotinate, 0.27%; in a 50/50 (v/v) isopropyl alcohol to water vehicle.
9. Axsain TM : A commercially available formulation sold as Axsain TM was topically applied 10 minutes prior to drug administration. Its ingredients include capsaicin, 0.075% in a washable ointment base.
10. Heet TM Liquid: A commercially available formulation sold as Heet TM was topically applied 10 minutes prior to drug administration. Its active ingredients include: Methyl salicylate, 15%; capsaicin, 0.025%; and camphor, 3.6% in 70% alcohol with acetone.

TABLE I

| EXAMPLE | DOG | PRETREATMENT |
|---|---|---|
| 1 | BO | GP-2-121-3 only - no vasodilator |
| 2 | PO | GP-2-121-3 only - no vasodilator |
| 3 | BO | 60° Heat; 10 minutes - no vasodilator |
| 4 | PO | 60° Heat; 10 minutes - no vasodilator |
| 5 | BO | 0.1% Tolazoline; Iontophoretic; 10 minutes |

TABLE I-continued

| EXAMPLE | DOG | PRETREATMENT |
|---|---|---|
| 6 | PO | 0.1% Tolazoline; Iontophoretic; 10 minutes |
| 7 | BO | 0.05% Pilocarpine; Iontophoretic; 10 minutes |
| 8 | PO | 0.05% Pilocarpine; Iontophoretic; 10 minutes |
| 9 | BO | 0.05% Methyl Nicotinate; Iontophoretic; 10 minutes |
| 10 | PO | 0.05% Methyl Nicotinate; Iontophoretic; 10 minutes |
| 11 | BO | Finalgon ® Topical Treatment; Throughout |
| 12 | PO | Finalgon ® Topical Treatment; Throughout |
| 13 | PO | Finalgon ® Topical Treatment; Throughout |
| 14 | BO | Omega ® Oil Topical Treatment; Throughout |
| 15 | PO | Omega ® Oil Topical Treatment; Throughout |
| 16 | PO | Omega ® Oil Topical Treatment; Throughout |
| 17 | PO | Omega ® Oil Topical Treatment; Throughout |
| 18 | BO | 0.1% Phenoxybenzamine; Iontophoretic; 10 minutes |
| 19 | PO | 0.1% Phenoxybenzamine; Iontophoretic; 10 minutes |
| 20 | BO | Axsain ™ Topical Treatment; Throughout |
| 21 | PO | Axsain ™ Topical Treatment; Throughout |
| 22 | BO | DCE 1 Topical Treatment; Throughout |
| 23 | PO | DCE 1 Topical Treatment; Throughout |
| 24 | BO | Heet ™ Liquid Topical Treatment; Throughout |
| 25 | PO | Heet ™ Liquid Topical Treatment; Throughout |

Referring to Table II the initial or baseline heart rate, is found in column 2 and is provided in beats per minute (bpm). In column 3, the highest or peak heart rate in bpm is shown. The change in heart rate from peak to baseline heart rate is shown in column 4. This change is the difference between the column 3 and column 2 heart rates, and is also given in bpm. In column 5, the time after start of delivery of the ESA ™ drug to the start of an increase in heart rate is shown. This time is labeled as the "onset time" and is given in units of minutes. Finally, in column 6, the slope of the line from baseline at the onset time to peak heart rate is provided. This slope is a measure of the rate of increase of the heart rate from the time when the increase began to the time when the peak heart rate was reached. The slope is given in units of beats per minute per minute.

All heart rate data in Table II as well as in the other Tables and in the Figures were smoothed before analysis to eliminate noise and outliers.

TABLE II

| Example | Baseline Heart Rate (Beats Per Minute) | Peak Heart Rate | Change in Heart Rate | Onset time (Minutes) | Onset Slope |
|---|---|---|---|---|---|
| 1 | 67 | 123 | 56 | 9.00 | 6.80 |
| 2 | 73 | 160 | 87 | 5.00 | 17.60 |
| 3 | 76 | 121 | 45 | 6.00 | 6.60 |
| 4 | 80 | 133 | 53 | 7.80 | 6.70 |
| 5 | 66 | 119 | 53 | 10.00 | 4.70 |
| 6 | 88 | 121 | 33 | 7.00 | 3.50 |
| 7 | 60 | 133 | 73 | 6.70 | 11.60 |
| 8 | 77 | 191 | 114 | 13.00 | 11.20 |
| 9 | 62 | 117 | 55 | 15.00 | 4.20 |
| 10 | 71 | 152 | 81 | 7.00 | 12.30 |
| 11 | 51 | 118 | 67 | 16.00 | 3.40 |
| 12 | 81 | 123 | 42 | 11.00 | 2.03 |
| 13 | 75 | 134 | 59 | 6.00 | 8.30 |
| 14 | 57 | 114 | 57 | 6.90 | 7.30 |
| 15 | 85 | 165 | 80 | 8.00 | 8.30 |
| 16 | 75 | 152 | 77 | 6.40 | 12.20 |
| 17 | 74 | 143 | 69 | 10.00 | 3.20 |
| 18 | 60 | 117 | 57 | 18.00 | 3.70 |
| 19 | 70 | 149 | 79 | 7.40 | 13.90 |
| 20 | 67 | 153 | 86 | 6.50 | 14.10 |
| 21 | 73 | 119 | 50 | 6.80 | 6.60 |
| 22 | 43 | 95 | 52 | 7.80 | 5.50 |
| 23 | 60 | 94 | 34 | 7.50 | 3.90 |
| 24 | 58 | 135 | 77 | 15.00 | 3.60 |
| 25 | 91 | 138 | 46 | 5.70 | 7.30 |

Referring to Table III, the elapsed time from when the ESA ™ drug delivery was stopped until the elevated heart rate returned to within 20 bpm of baseline is listed in column 2 for each example. This column has been labeled "offset time" and is the experimental value of the offset time defined previously. The value 20 bpm above baseline was selected arbitrarily, but is believed to provide an accurate standard from which to make accurate comparisons between the various formulations and methods tested. The value 20 bpm above baseline is also relatively small in relation to the peak heart rate.

Column 3 lists the slope of the line from the point corresponding to the time of ESA ™ drug delivery shut-off to the time corresponding to when 20 bpm above baseline heart rate was reached. Columns 4-6 provide the slope of the offset time in three components, i.e., from 0-5 minutes after the heart rate begins to decline; from 5-10 minutes after decline begins; and from 10-30 minutes after decline begins. The slope in each of columns 3-6 is given in units of beats per minute per minute and provides a measure of the rate at which the heart rate is slowing down during each interval. The column 2 slope is a measure over the entire period, whereas the columns 4-6 slopes provide this measure in increments of interest.

Columns 7-9 provide the time when the ESA ™ drug was shut-off, when the elevated heart rate began to decline and the elapsed time of delay between when the drug was shut-off and the heart rate began to decline.

TABLE III

| Example | Offset time (minutes) | Offset Slope | Offset Slope Components (0–5) min | (5–10) min | (10–30) min | Time Drug Off (min) | Time Start Decline (min) | Delay (min) |
|---|---|---|---|---|---|---|---|---|
| 1 | 29.00 | −0.30 | −0.40 | −0.80 | −0.02 | 12.50 | 14.00 | 1.50 |
| 2 | 39.00 | −0.25 | −3.70 | 1.70 | −0.50 | 5.50 | 12.50 | 7.00 |
| 3 | 27.00 | −0.60 | −2.80 | 0.27 | −0.43 | 8.00 | 8.00 | 0.00 |
| 4 | 22.00 | −1.20 | −2.70 | −0.21 | −0.24 | 7.40 | 11.40 | 4.00 |
| 5 | 34.00 | −1.00 | −0.90 | −3.30 | −0.70 | 18.00 | 20.00 | 2.00 |
| 6 | 8.00 | −3.20 | −1.40 | −3.90 | −0.58 | 17.00 | 21.00 | 4.00 |
| 7 | 38.00 | −1.10 | −1.70 | −2.50 | −1.10 | 22.50 | 23.80 | 1.30 |
| 8 | 36.00 | −1.70 | −7.60 | −1.40 | −1.00 | 19.00 | 24.30 | 5.30 |
| 9 | 29.00 | −0.40 | −2.40 | −0.40 | −0.28 | 18.50 | 25.00 | 6.50 |
| 10 | 31.00 | −1.70 | −1.40 | −2.40 | −1.90 | 18.00 | 20.50 | 2.50 |
| 11 | 40.00 | −1.00 | −1.30 | −2.60 | −1.00 | 8.00 | 19.50 | 11.50 |

TABLE III-continued

| Example | Offset time (minutes) | Offset Slope | Offset Slope Components | | | Time Drug Off (min) | Time Start Decline (min) | Delay (min) |
|---|---|---|---|---|---|---|---|---|
| | | | (0–5) min | (5–10) min | (10–30) min | | | |
| 12 | 12.00 | −3.20 | −6.30 | −1.40 | −0.30 | 21.00 | 26.50 | 5.50 |
| 13 | 19.40 | −0.04 | −1.90 | −1.50 | 0.63 | 7.50 | 10.50 | 3.00 |
| 14 | 36.00 | −1.10 | −1.20 | −2.40 | −0.74 | 7.50 | 14.50 | 7.00 |
| 15 | 27.00 | −1.90 | −5.40 | −4.40 | −0.87 | 7.00 | 10.00 | 3.00 |
| 16 | 25.00 | −2.30 | −3.90 | −4.30 | −1.60 | 7.00 | 10.00 | 3.00 |
| 17 | 15.00 | −3.30 | −4.90 | −0.90 | −1.60 | 10.50 | 13.50 | 3.00 |
| 18 | 30.00 | −0.80 | −4.20 | 0.02 | −0.53 | 18.00 | 28.00 | 10.00 |
| 19 | 25.80 | −2.30 | −4.90 | −2.00 | −1.80 | 18.50 | 22.00 | 3.50 |
| 20 | 20.20 | −1.30 | −1.70 | −2.40 | −0.10 | 10.40 | 11.50 | 1.10 |
| 21 | 33.80 | −0.80 | −0.50 | −1.30 | −0.30 | 7.00 | 10.00 | 3.00 |
| 22 | 22.60 | −1.20 | −1.20 | −1.90 | −0.48 | 17.00 | 27.10 | 10.10 |
| 23 | 11.60 | −1.80 | −4.00 | −0.08 | −0.02 | 8.60 | 14.20 | 5.60 |
| 24 | 13.00 | −1.70 | −2.30 | 1.10 | −0.50 | 7.50 | 37.00 | 29.50 |
| 25 | 16.90 | −2.40 | −5.40 | −2.80 | −0.40 | 7.00 | 8.60 | 1.60 |

Referring to Table IV, the half-life and notes are provided regarding the half-life of the elevated heart rate decay, or decline. The half-life is listed in column 2 as "t ½", referring to the half-life of the decay of the elevated heart rate.

TABLE IV

| Example | t ½d | Total time (startup) thru offset plateau |
|---|---|---|
| 1 | | Never reached to w/in 20 bpm of baseline. |
| 2 | | Never reached to w/in 20 bpm pf baseline |
| 3 | 12.00 | Never reached to w/in 20 bpm of baseline. |
| 4 | 11.76 | W/in 20 at 22 min.; reached baseline at 43 min. |
| 5 | 14.06 | W/in 20 at 34 min.; reached baseline at 60 min. |
| 6 | 6.77 | Reached baseline at 30 min. |
| 7 | 28.85 | Never reached w/in 20 bpm of baseline. |
| 8 | 21.36 | W/in 20 bpm of baseline at 60 min. |
| 9 | | Never Reached w/in 20 bpm of baseline. |
| 10 | 21.36 | W/in 20 bpm of baseline at 55 min.; never lower. |
| 11 | 20.60 | W/in 20 bpm of baseline at 55 min. and decreasing. |
| 12 | 2.86 | Reached baseline at 30 min. |
| 13 | | Never reached w/in 20 bpm of baseline. |
| 14 | 17.47 | Reached w/in 20 bpm of baseline in 36 min. |
| 15 | 7.10 | Reached baseline at 30 min. |
| 16 | 10.29 | W/in 10 bpm of baseline in 35 min. |
| 17 | 8.47 | W/in 20 bpm of baseline in 29 min. and decreasing. |
| 18 | 16.96 | W/in 10 bpm of baseline in 60 min. |
| 19 | 11.52 | W/in 10 bpm of baseline in 48 min. |
| 20 | | Never reached to w/in 20 bpm of baseline. |
| 21 | 7.67 | W/in 10 bpm of baseline in 42 min. |
| 22 | 16.47 | W/in 20 bpm of baseline in 50 min. and decreasing. |
| 23 | 7.02 | W/in 5 bpm of baseline in 26 min. |
| 24 | | Never reached w/in 20 bpm of baseline. |
| 25 | 5.53 | Reached baseline at 26 min. |

Referring to Tables I–IV, the important variables for this analysis are:
1. The delay between time where drug administration stopped and start of decline in heart rate, as shown in Table III, column 9, "Delay."
2. The slope of heart rate decline in three consecutive segments: 0–5, 5–10 and 10–30 minutes after the start of decline, as shown in Table III, columns 4–6, "Offset Slope Components."
3. The half life, in minutes, of the heart rate decline obtained from an exponential fit to the data, as shown in Table IV, column 2, "t ½."

Referring to the FIG. 1 bar graph the percent decline in elevated heart rate for each of the Table III intervals (0–5), (5–10) and (10–30) is graphically shown for the control and for each of the different pretreatments. Standard deviation error bars are also shown extending from the bar representing each of the intervals. The values were calculated from the slopes set forth in Table III, columns 4–6 and delay to onset of decline as listed in Table III, column 9.

As shown in FIG. 1 the greatest percent decline in heart rate was produced in the 10–20 minute interval with the iontophoretically pre-delivered totazoline. The next greatest percent decline was produced in the 10–20 minute interval with the topically applied Omega ® Oil formulation. The topically applied Heet ™ formulation provided the third highest percent decline.

In the 5–10 minute interval topically applied Heet ™ formulation provided the greatest percent decline, with topically applied Omega ® Oil and iontophoretically pre-delivered pilocarpine resulting in the next highest percent declines in heart rate.

In the 0–5 minute interval the Heet ™ formulation, simple heat and the Omega ® Oil formulation provided the three greatest percent declines in heart rate.

Based on these data and calculations, the Omega ® Oil and Heet ™ formulations appear to be the most efficient formulations for reducing the depot over the intervals of interest.

Figure 2:
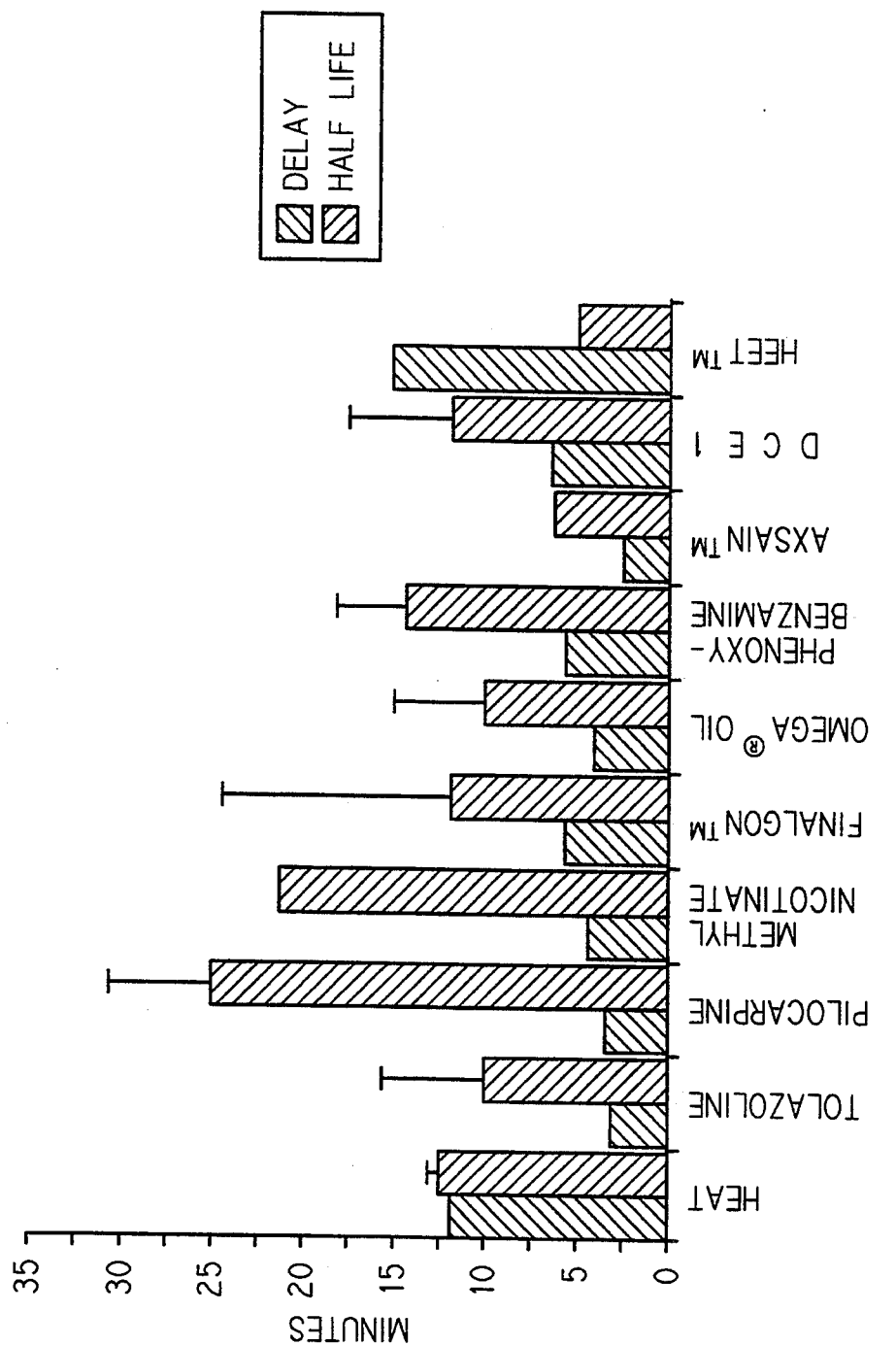
FIG. 2 is a bar graph illustrating the half life of heart rate decay and the delay time associated with various vasodilator formulations of the present invention compared to a control.

Referring to the FIG. 2 bar graph, the heart rate decay half-lives and the delay to onset of heart rate decline are shown in minutes. As shown in FIG. 2, topical pretreatment with Heet ™ formulation produced the shortest half-life, and topical pretreatment with Axsain ™ and Omega ® Oil formulations, and iontophoretic pre-treatment with tolazoline produced relatively short half-lives compared to iontophoretically preadministered pilocarpine and methyl nicotinate.

Referring to the "delay" as shown in FIG. 2, it may be seen that Axsain ™ formulation, tolazoline, pilocarpine and Omega ® Oil formulations provided the shortest delay between shut off of drug transport from the electrode to onset of heart rate decline.

Figure 3:
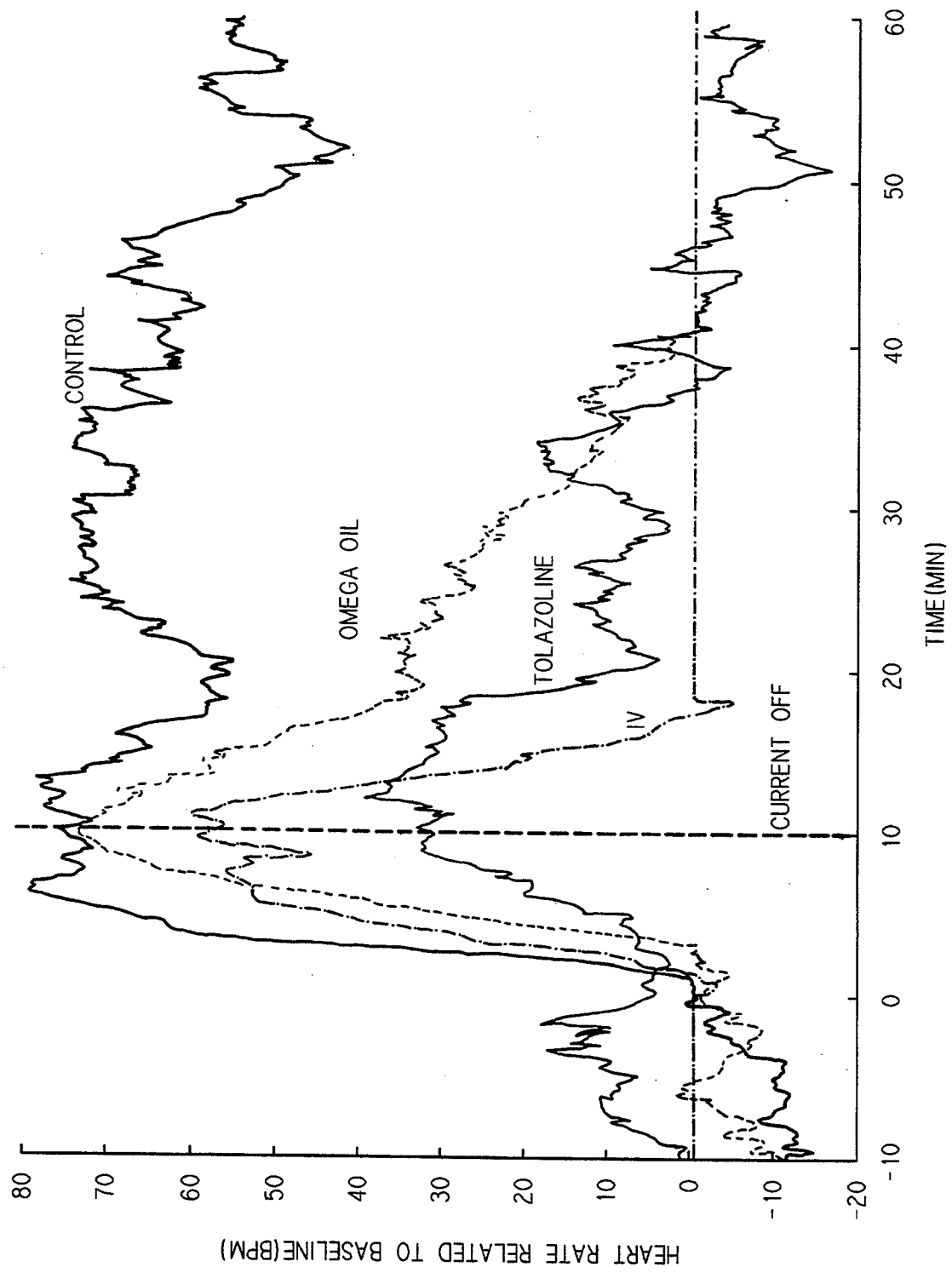
FIG. 3 is a plot of the effect of pretreatments of two vasodilator formulations of the present invention on offset time for the first test subject dog compared to a control and compared to IV administration of a test drug.
Figure 4:
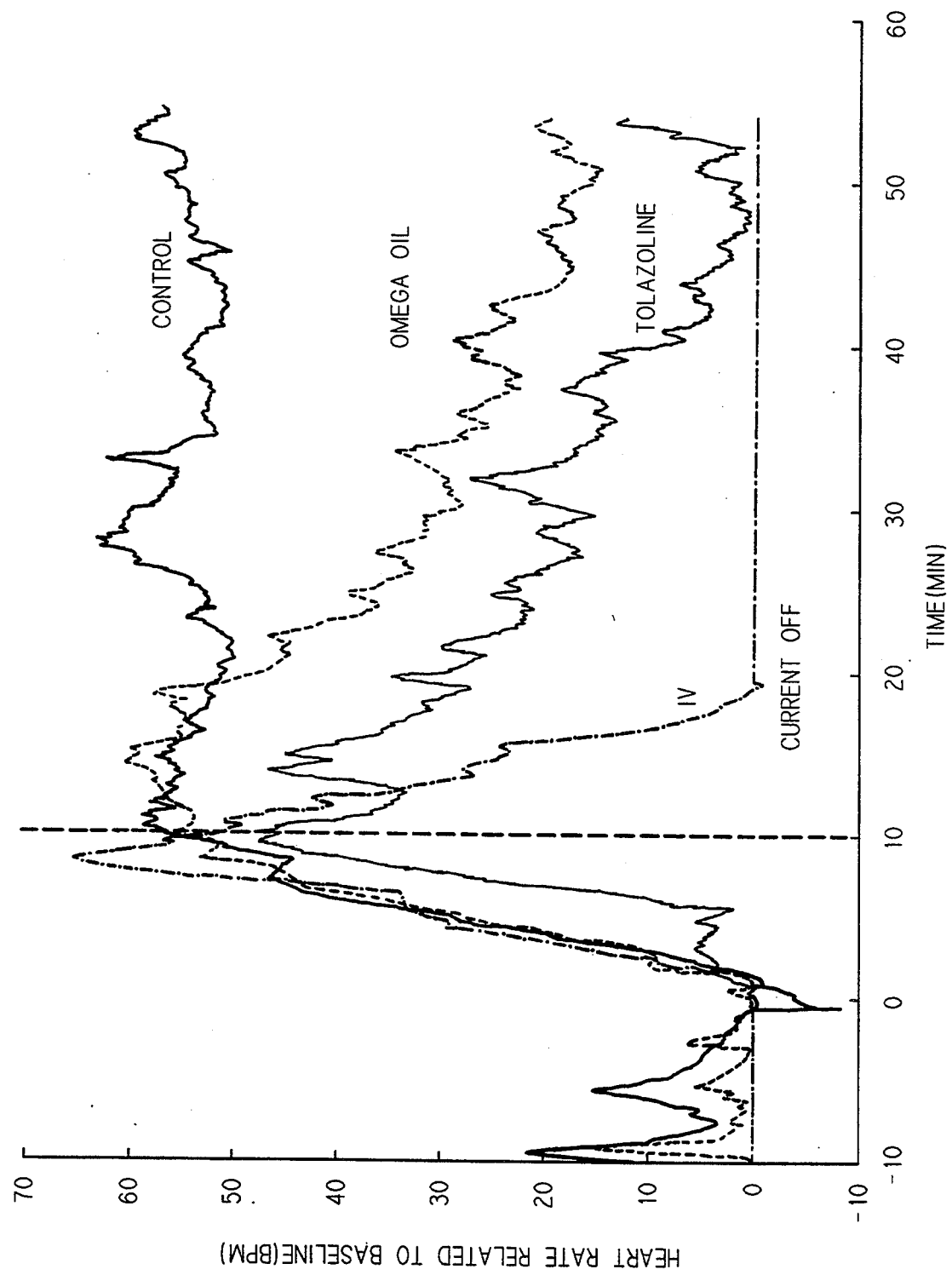
FIG. 4 is a plot of the effect of pretreatments of two vasodilator formulations of the present invention on offset time for the second test subject dog compared to a control and compared to IV administration of a test drug.

To better visualize the significance of the effect on elevated heart rate, FIGS. 3 and 4 display the elevated heart rate data against time for each dog for the control data run, the Omega ® Oil topical pretreatment and the tolazoline iontophoretic pretreatment.

Also plotted in FIGS. 3 and 4 is the heart rate over time resulting from an IV administration of the ESA ™ drug. Referring to FIG. 3, dog "PO", 0.08 microgram of GP 2-121-3 per kilogram of dog body weight per minute was administered over a 7 minute period. Referring to FIG. 4, dog "BO", 0.10 microgram of GP 2-121-3 per kilogram per minute was administered over a 10 minute period. Based on other preclinical and clinical studies using intravenous (IV) infusion of an ESA TM drug, the pharmacokinetic and phamacodynamic half-life of the drug has been calculated to be about 7 minutes. Also, a similar decay in heart rate was observed using the IV route of administration. Thus, the fastest decline in heart rate, i.e., fastest reduction in offset possible is that associated with the IV route of administration of the ESA TM drug as illustrated in the FIGS. 3 and 4 "IV" plots. However, because IV administration is invasive, and for other reasons relating to convenience, IV administration of ESA TM drug is not as preferred as iontophoretic administration in many environments and thus has no bearing on the present invention except to produce one extreme reference point.

At the other extreme in FIGS. 3 and 4 is the control run, i.e., the plot from data taken with no application of vasodilator or alpha blocker. The control data plot demonstrates essentially no reduction in heart rate over the data collection time.

Between the extremes the Omega ® Oil formulation and tolazoline pre-treatments demonstrate dramatic reduction in heart rate offset and illustrate the degree of dermal clearance enhancement resulting from the present invention. As indicated in FIGS. 3 and 4, the current was shut off 10 minutes after ESA TM drug administration began.

Example B

Experiments on Human Volunteers

Experiments were conducted on human volunteers to determine the degree of vasodilation/irritation of various formulations, and thus their expected usefulness as preferred formulations of the present invention.

In these experiments data were collected from seven human volunteers concerning the effects of topical dermal clearance enhancers. The dermal clearance enhancers tested were all components of Omega ® Oil, an over-the-counter arthritis relief formula. All subjects' right arms were treated with eleven formulations, identified as Examples 26-36 in the following Table V. Approximately 0.5 ml of each formulation was topically applied with a cotton applicator to a 2cm² area of skin on the volar surface of the arm. Observations were recorded at 10, 20, and 30 minute intervals. The following redness/irritation index was used to categorize vasodilation/irritation:

0 = no redness, i.e., erythema;
1 = some redness;
2 = pronounced redness;
W = Wheal irritation, i.e., edemic core surrounded by an erythemic ring; and
WH = whitening.

TABLE V

Vasodilator Formulations Applied to Human Subjects

| Example | Identity | Ingredients |
|---|---|---|
| 26 | Omega ® oil | Methyl-salicylate, 17.5%; histamine dihydrochloride, 0.02%; methylester of nicotinic acid, 0.27%; and capsicum oleoresin, 0.24% in a 50/50 (v/v) isopropyl alcohol to water vehicle. |
| 27 | HEET TM Liquid | Methyl Salicylate, 15.0%; capsaicin, 0.025% and camphor, 3.6% in 70% alcohol with acetone. |
| 28 | DCE 1 | Capsaicin, 0.24% and methyl nicotinate 0.27% in a 50/50 (v/v) isopropyl alcohol to water vehicle. |
| 29 | DCE 3 | 0.24% Capsaicin in 70% ethyl alcohol. |
| 30 | DCE 4 | 0.24% Capsaicine in 70% ethyl alcohol. |
| 31 | DCE 5 | 0.24% Methyl nicotinate in 70% ethyl alcohol. |
| 32 | DCE 2 | .02% Histamine dihydrochloride in a 50/50 (v/v) isopropyl alcohol water vehicle. |
| 33 | Vehicle | 70% Ethyl alcohol. |
| 34 | Vehicle | 50/50 (v/v) Isopropyl alcohol to Millipore Q water. |
| 35 | HEET TM Spray | Methyl Salicylate, 25%; camphor, 3%; menthol, 3%; and 1% methyl nicotinate in an isopropyl alcohol vehicle. |
| 36 | Methyl Salicylate | 99+% Methyl salicylate. |

The presence of vasodilation was determined by degree of redness of the skin. Wheal irritation was signified by the presence of an erythemic ring surrounding an upraised pale center. Whitening was denoted by a pale area with no upraising or redness. The resulting index scores were recorded and Table VI presents these averaged scores. Referring to Table VI, an index score of 2-W, for example, indicates pronounced redness and Wheal irritation.

Based on the results shown in Table VI, formulation Examples 26, 28, 31 and 35 exhibited the greatest vasodilation in this subject group. All three of these formulations contained one common ingredient, methyl nicotinate. All four formulations were in alcohol vehicles. Based upon the lack of a redness response in treatment Example 33, ethyl alcohol and Example 34, isopropyl alcohol, it appears that the alcohol vehicle serves no vasodilatory function. In the majority of subjects, a 10 minute time period was adequate for maximal erythemic response to the dermal clearance enhancers.

TABLE VI

Results of Vasodilator Formulations Applied to Human Subjects

| Example | Time Period (min.) | TS | UM | CV | RT | JP | WB | RH | Mean |
|---|---|---|---|---|---|---|---|---|---|
| 26 | 10 | 2 | 2 | 1 | 2 | 2 | 0 | 1 | 1.4 |
|    | 20 | 2 | 2-R | 2 | 1 | 2 | 0 | 2 | 1.6 |
|    | 30 | 2 | 2-R | 2 | 1 | 2 | 0 | 2 | 1.6 |
| 27 | 10 | 0 | E | 0 | 0 | 0 | E | 0 | 0 |
|    | 20 | 1-R | E | 0 | 0 | 0 | E | 0 | 0.1 |
|    | 30 | 1-R | E | 0 | 0 | 0 | E | 0 | 0.1 |
| 28 | 10 | 2 | 2-R | 2 | 1 | 2 | E | 2-R | 1.6 |
|    | 20 | 2 | 2-A | 2 | 1 | 2-A | E | 2-A | 1.6 |
|    | 30 | 2 | 2-A | 2 | 1-A | 2-A | E | 2-R | 1.6 |
| 29 | 10 | 0 | 1 | 0 | 0 | 0 | 0 | 0 | 0.1 |
|    | 20 | 0 | 1 | 0 | 0 | 0 | 0 | 0 | 0.1 |
|    | 30 | 0 | 1 | 0 | 0 | 0 | 0 | 0 | 0.1 |

TABLE VI-continued

Results of Vasodilator Formulations Applied to Human Subjects

| Example | Time Period (min.) | TS | UM | CV | RT | JP | WB | RH | Mean |
|---|---|---|---|---|---|---|---|---|---|
| 30 | 10 | 0 | 0 | 0 | 0 | 0 | E | 0 | 0 |
|  | 20 | 0 | 0 | 0 | 0 | 0 | 0 | 0 | 0 |
|  | 30 | 0 | 0 | 0 | 0 | 0 | 0 | 0 | 0 |
| 31 | 10 | 2 | 2-A | 2 | 1 | 2 | 1-A | 2 | 1.7 |
|  | 20 | 2 | 2-A | 2 | 1 | 2-R | 1-A | 2-A | 1.7 |
|  | 30 | 2 | 2-A | 2 | 1 | 2-A | 1-A | 2-A | 1.7 |
| 32 | 10 | 0 | 0 | 0 | 0 | 0 | 0 | 0 | 0 |
|  | 20 | 0 | 0 | 0 | 0 | 0 | 0 | 0 | 0 |
|  | 30 | 0 | 0 | 0 | 0 | 0 | 0 | 0 | 0 |
| 33 | 10 | 0 | 0 | 0 | 0 | 0 | 0 | 0 | 0 |
|  | 20 | 0 | 0 | 0 | 0 | 0 | 0 | 0 | 0 |
|  | 30 | 0 | 0 | 0 | 0 | 0 | 0 | 0 | 0 |
| 34 | 10 | 0 | 0 | 0 | 0 | 0 | 0 | 0 | 0 |
|  | 20 | 0 | 0 | 0 | 0 | 0 | 0 | 1 | 0.1 |
|  | 30 | 0 | 0 | 0 | 0 | 0 | 0 | 1 | 0.1 |
| 35 | 10 | 2-W | 2-W | 1 | WH | 2 | 2 | 1 | 1.4 |
|  | 20 | 2-W | 2-W | 2 | WH | 2 | 2 | 2 | 1.7 |
|  | 30 | 2-W | 2-W | 1 | WH | 2-W | 2 | 1 | 1.4 |
| 36 | 10 | 0 | 0 | 0 | WH | 0 | 0 | WH | 0 |
|  | 20 | WH | WH | 0 | WH | 0 | 0 | WH | 0 |
|  | 30 | WH | WH | 0 | WH | 0 | 0 | WH | 0 |

The above-described preferred embodiments and examples have been disclosed for illustration purposes and not for purposes of limitation. It will be recognized that variations in the above-described formulations, methods and systems are possible and that the present invention is not to be limited to the preferred embodiments and examples disclosed, but rather as set forth in the claims appended hereto.

Example C

Additional In Vivo Dog Experiments

Additional experiments were performed to study the effect of certain compositions on the offset time and dermal clearance in dogs.

In these experiments, the formulation to be tested was applied either topically or by transdermal iontophoresis (TDI) as described below. After the pretreatment period, arbutamine was applied using TDI for 10 minutes as described below. the formulations tested are as follows:

Iontophoretically Applied Formulations

Methyl Nicotinate: (Sigma Chemical Co.): 0.05% methyl nicotinate was formulated in a water-soluble gel consisting of Methocel TM E10M (hydroxypropyl methyl cellulose, Dow Chemical Company) as the gelling agent.

Phenoxybenzamine Hydrochloride (Spectrum Chemical Co.): 0.10% phenoxybenzamine was formulated in a water-soluble gel consisting of Methocel TM E10M (hydroxypropyl methyl cellulose, Dow Chemical Company) as the gelling agent.

Phentolamine Hydrochloride (Sigma Chemical Co.): 1.00% phentolamine was formulated in a water-soluble gel consisting of Methocel TM E10M (hydroxypropyl methyl cellulose, Dow Chemical Company) as the gelling agent.

Pilocarpine Hydrochloride (Spectrum Chemical Co.): 0.05% pilocarpine was formulated in a water-soluble gel consisting of Methocel TM E10M (hydroxypropyl methyl cellulose, Dow Chemical Company) as the gelling agent.

Tolazoline Hydrochloride (Sigma Chemical Co.): 1.00% tolazoline was formulated in a water-soluble gel consisting of Methocel TM E10M (hydroxypropyl methyl cellulose, Dow Chemical Company) as the gelling agent.

Topically Applied Formulations

Alpha Oil: (Gensia Pharmaceuticals, Inc.): 0.27% (w/w) Methyl nicotinate (Sigma Chemical Co.), 0.24% Capsicum oleoresin (Whitehall/McFalan Smith Ltd., Edinborough, Scotland) and 0.02% Histamine dihydrochloride (Sigma Chemical Co.) in a vehicle consisting of 2.9:2.0:1.0 isopropyl alcohol, light Mineral oil (Sigma Chemical Co.), and Methyl salicylate (Aldrich Chemical Co.).

Axsain TM (Galen Pharma, Inc.): 0.075% Capsaicin in a vehicle consisting of Benzyl alcohol, Cetyl alcohol, Glyceryl monostearate, Isopropyl myristate, Polyoxyethylene stearate blend, purified water, Sorbitol, and white petrolatum.

Beta Oil: (Gensia Pharmaceuticals, Inc.): 0.27% (w/w/Methyl nicotinate (Sigma Chemical Co.), 0,028% Capsaicin (Sigma Chemical Co.) and 0.02% Histamine dihydrochloride (Sigma Chemical Co.) in a vehicle consisting of 2.9:2.0:1.0 isopropyl alcohol, light Mineral oil (Sigma Chemical Co.), and Methyl salicylate (Aldrich Chemical Co.).

DCE1: (Gensia Pharmaceuticals, Inc.): 0.27% Methyl nicotinate (Sigma Chemical Co.), 0.24% Capsaicin (Sigma Chemical Co.) in 50/50 (v/v/) isopropyl alcohol to water.

DCE2: (Gensia Pharmaceuticlas, Inc.): 0.02% Histamine dihydrochloride (Sigma Chemical Co.) in 50/50 (v/v) isopropyl alcohol to water.

DCE3: (Gensia Pharmaceuticals, Inc.): 0.24% Capsaicin (Sigma Chemical Co.) in 70% Ethyl Alcohol.

DCE4: (Gensia Pharmaceuticals, Inc.): 0.24% Capsaicine (sigma Chemical Co.) in 70% Ethyl Alcohol.

DCE5: (Gensia Pharmaceuticals, Inc.): 0.24% Methyl nicotinate (Sigma Chemical Co.) in 70% Ethyl alcohol.

DCE6: (Gensia Pharmaceuticals, Inc.): 0,075% Capsaicin (Sigma Chemical Co.), 0.27% Methyl nicotinate (Sigma Chemical Co.) in 50/50 (v/v) isopropyl alcohol to water.

Delta Oil: (Gensia Pharmaceuticals, Inc.): 0.27% (w/w) Methyl nicotinate (Sigma Chemical Co.), 0.028% Capsairin (Sigman Chemical Co.) in a vehicle consisting of 2.9:2.0:1.0 ethyl alcohol, propylene glycol and methyl salicylate (Aldrich Chemical Co.).

Finalgon ™ (Dr. Karl Thomae GmbH): 0.40% Nonivamide and 2.5% Butoxyethyl nicotinate in an ointment base.

Gamma Oil: (Gensia Pharmaceuticals, Inc.): 0.27% (w/w) Methyl nicotinate (Sigma Chemical Co.), 0,280% Capsaicin (Sigma Chemical Co.) in a vehicle consisting of 2.9:2.0:1.0 isopropyl alcohol, light Mineral oil (Sigma Chemical Co.) and Methyl salicylate (Aldrich Chemical Co.).

Heet ™ Liniment (Whitehall Laboratories): 15.0% Methyl salicylate, 3.6% Camphor, 0.025% Capsaicin in Acetone and 70% alcohol.

Omega ® Oil (Block Drug Co. Jersey City, N.J.): 0.02% Histamine dihydrochloride, 17.5% Methyl salicylate, 0.27% Methyl nicotinate, 0.24% Capsicum oleoresin in a vehicle consisting of Mineral oil and Isopropyl alcohol (IPA).

Rubriment ® (Nordmark): 2.0% Benzyl nicotinate, 0.2% Salicylamide, 1.8% (2-Hydroxyethyl)-salicylate, 3.0% Turpentine oil, 3.0% Camphor, 0.1% Nonivamide.

Heat: A hot pack (Heat Comfort ™, 3M Consumer Specialties Division) was warmed to 60° C.

Animal Preparation and handling

Six labrador dogs (20 to 30 kg) were trained to lie quietly on a table. Before each experiment, three ECG electrodes (one lead) were applied on shaved areas of the back (near the front legs) to obtain the heart rate. The outer hind leg area (either right or left) was shaved prior to each experiment, with care taken not to cut or visibly damage the skin. The area was cleaned with soap and water and the skin was then deflated using an alcohol swab followed by skin preparation with 3M One-Step-Prep ™ tape.

Pretreatment

Each vasodilator that was delivered by TDI used a 1.8 cm$^2$ electrode (Graphic Controls, Buffalo, N.Y.) containing the vasodilator in a gel at the concentrations listed in experimental methods section. In all experiments, an indifferent electrode containing a phosphate-buffered-saline gel was applied to the skin in conjunction with the electrode containing the vasodilator. Each vasodilator tested was applied for 10 minutes using a current of 0.6 mA/cm$^2$. During this time the heart rate was continuously recorded (at 5 second intervals) with the ESA Research System. The delivery electrodes were then removed, and any excess gel adhering to the skin was gently removed using a tissue.

Each topically applied vasodilator was applied to the skin in a volume of approximately 0.25 ml. The agent was allowed to absorb into the skin, during which time the heart rate was continuously recorded for 10 minutes using the ESA Research System.

To test if heat alone would produce sufficient vasodilation, a 60° C. hot pack was applied to the skin 10 minutes prior to drug delivery, during which time the heat rate was continuously recorded by the ESA System. Once drug delivery electrodes were applied, the heat pack was reheated and placed on top of them for the duration of the study.

Arbutamine Administration

Following the 10 minute pretreatment period, a 48mM arbutamine electrode and indifferent electrode were applied and drug delivery was initiated. A current density of 1.0 mA/cm$^2$ was delivered for 10 minutes to yield a dose[1] (ITCA) of 30.6. The purpose of this treatment was to produce an elevated heart rate response of at least 40 beats-per-minute above baseline lasting for at least 30 minutes.

---
[1] The dose (ITCA) was calculated by multiplying the applied current density (mA/cm$^2$) by the duration of delivery (minutes) and the drug concentration (%) and the area of the electrode (cm$^2$). This has been shown to correlate with the rate of drug delivery ($\mu$g/cm$^2$/hr) from the electrode (23). The units of ITCA are mA.minutes.

Results

FIGS. 3 and 4 show the effect of pretreatment with two different vasodilator formulations on the offset time in two separate dogs. The curve labelled "control" demonstrates the prolonged elevation of heart rate following TDI delivery of arbutamine without pretreatment. The other curves demonstrate the response following pretreatment with either iontophoretically applied tolazoline or topically applied Omega ® Oil. The response following intravenous administration at an infusion rate of 0.06 and 0.08 $\mu$g/kg/min, respectively, was included to demonstrate the fastest possible arbutamine response in that animal.

After recognizing the vasodilators' potential for dermal clearance enhancement, variables for analysis were chosen to compare these pretreatments. The rate of rise (onset) was fairly consistent and unaffected by the presence of vasodilators. The important variables for this analysis are:

1) delay between time when drug administration was stopped and start of decline in heart rate;
2) the time (minutes) to reach successive percent levels (i.e. 10, 20, 30, 40, and 50% decline) from the point of maximum change in heart rate[2].
3) the half-life (minutes) of the heart rate decline obtained from an exponential fit of the offset slope.

Figure 5:
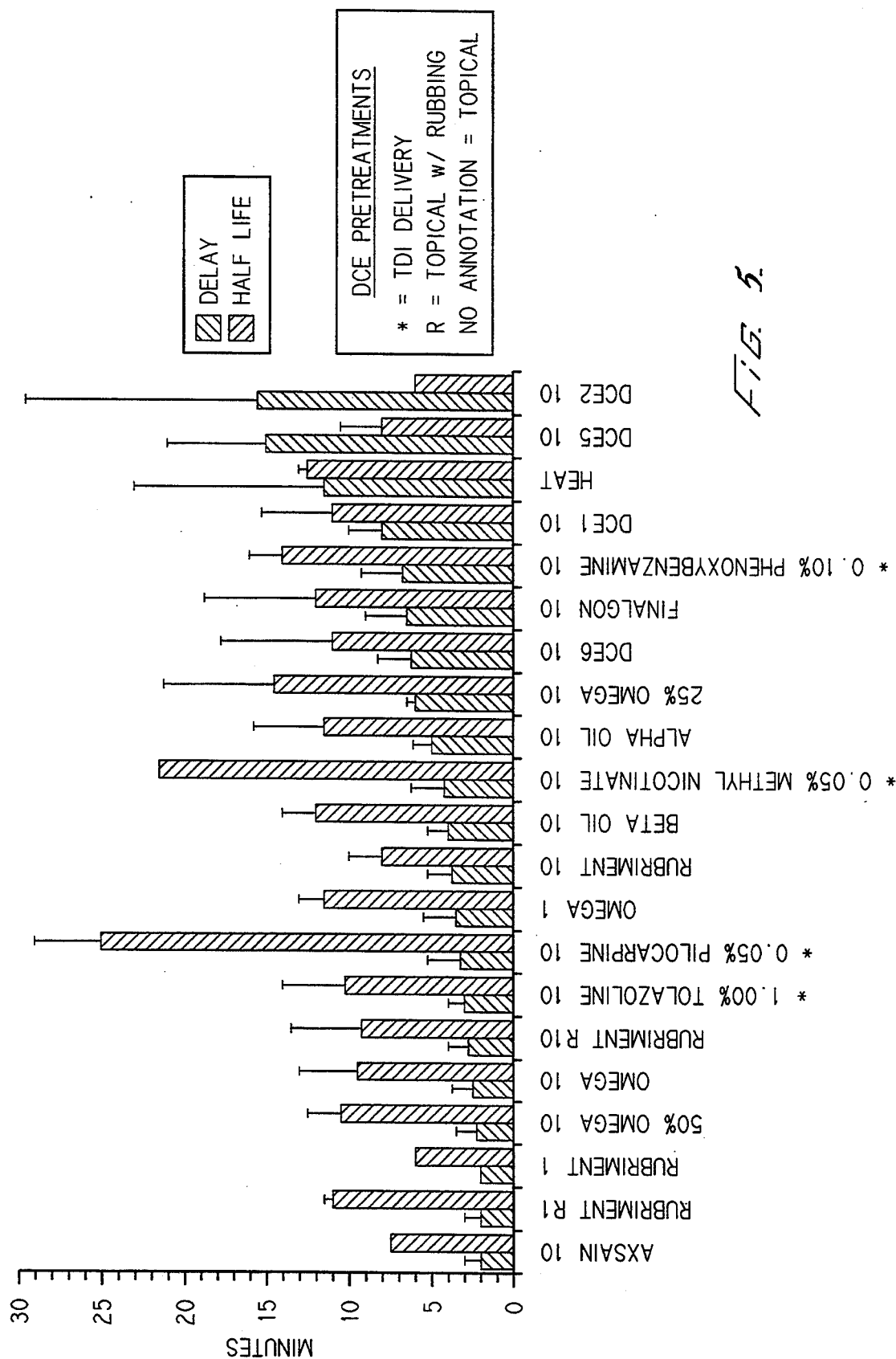
FIG. 5 is a bar graph illustrating the in vivo pharmacodynamic delay and half-life of dermal clearance enhancer formulations.

A combination of over-the-counter (OTC) and proprietary formulations were selected for comparison. FIG. 5 is a bar graph illustrating the half-life and delay time associated with the application of a variety of OTC and proprietary formulations compared to control. As indicated in FIG. 5, both TDI and topical vasodilator (i.e. dermal clearance enhancer) formulations were included in the study. Following the dermal clearance enhancer (DCE) name is a suffix which signifies whether the formulation was rubbed into the skin (R) (i.e. applied topically) or applied by transdermal iontophoresis, and the pretreatment time (e.g. 1 or 10 minutes). Two dogs received each treatment at least one time. The agents (i e , Omega ® Oil, Rubriment ®, Tolazoline) that demonstrated the most pronounced response in these animals, were tested in an additional two animals for n=4 per treatment.

Figure 6:
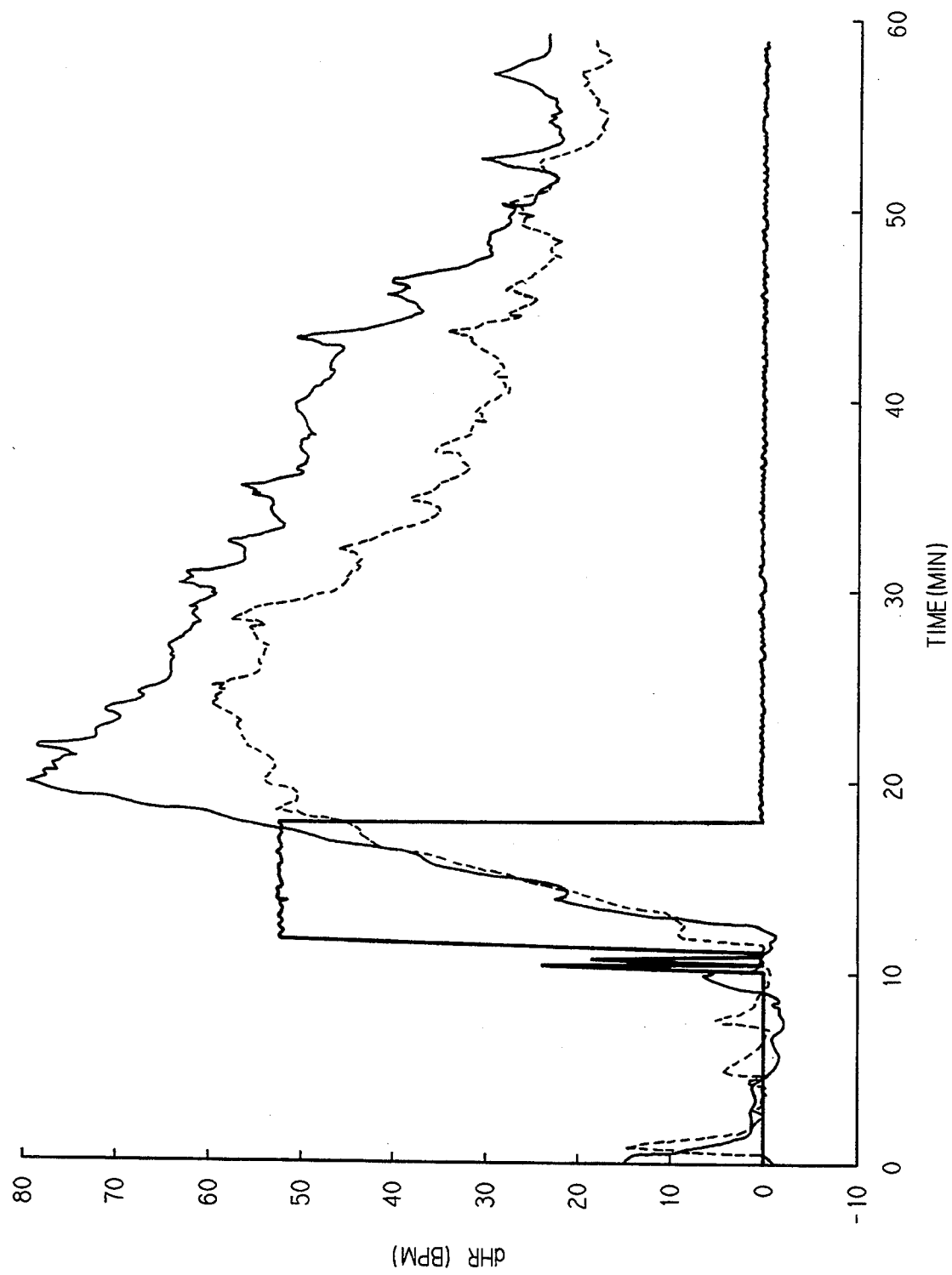
FIGS. 6 and 7 are plots depicting the reproducibility of pre-treatment with one of the tested formulations (Omega Oil ®) on a test dog. (BO-FIG. 6, PO-FIG. 7).
Figure 7:
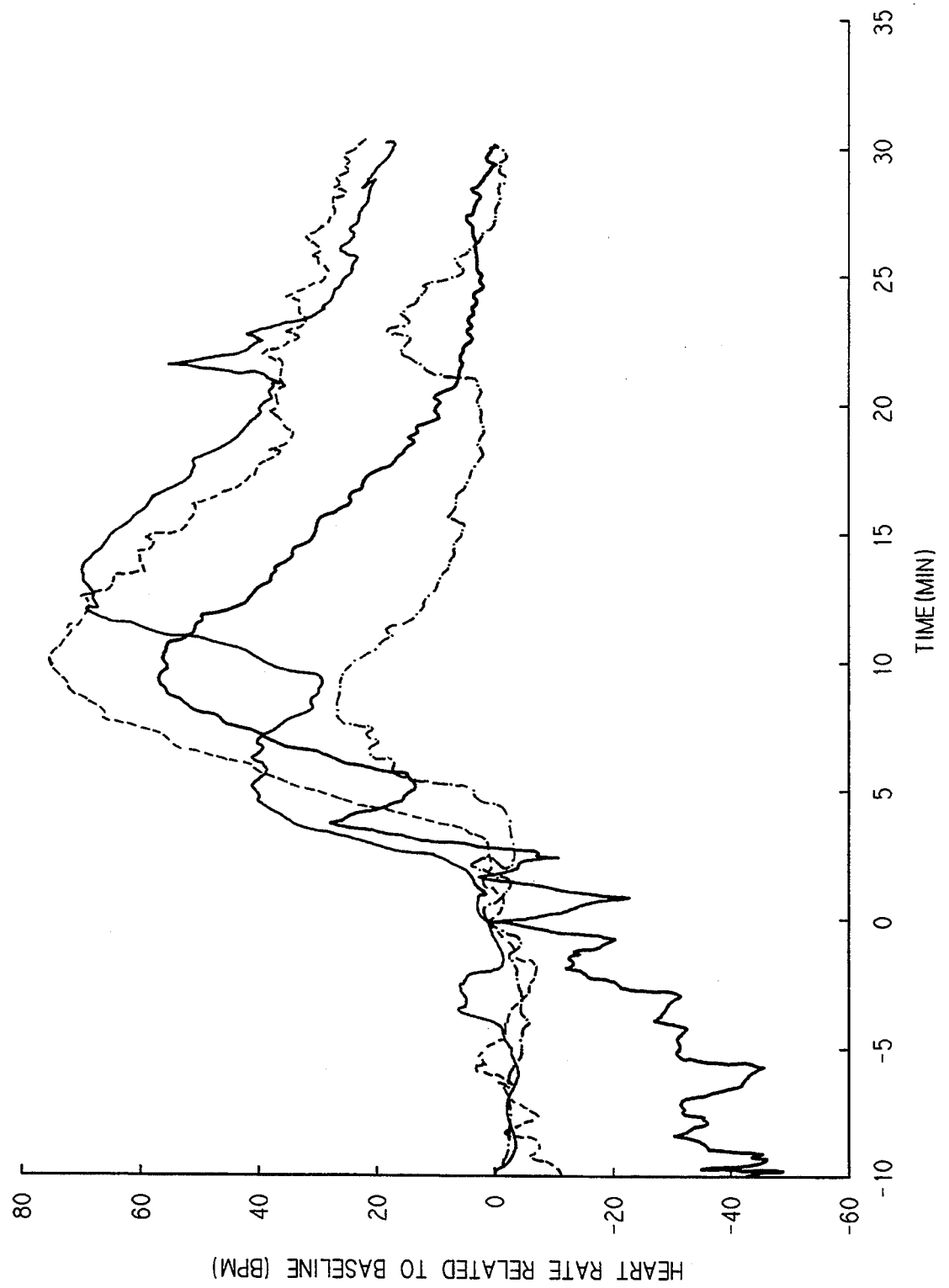

Omega ® Oil was tested multiple times in each animal to examine the reproducibility of the response. FIGS. 6 and 7 are graphs of the change in heart rate versus time, for a single animal (either PO or BO) receiving the same regimen (e.g., pretreatment with Omega ® Oil followed by TDI arbutamine) on different days.

After completion of this DCE screening study, the formulations which exhibited the shortest delay and half-life, as well as the most rapid decline in heart rate (offset) were tested for a total of twelve treatments (6 dogs, each receiving two treatments). Table 7 summarizes the variables calculated for this analysis. The six dogs are identified in the table as BA, BB, BO, MI, PO and SA, followed by the experimental identification number. These dogs received control (no pretreatment) and five DCE pretreatment regimens.

Figure 8:
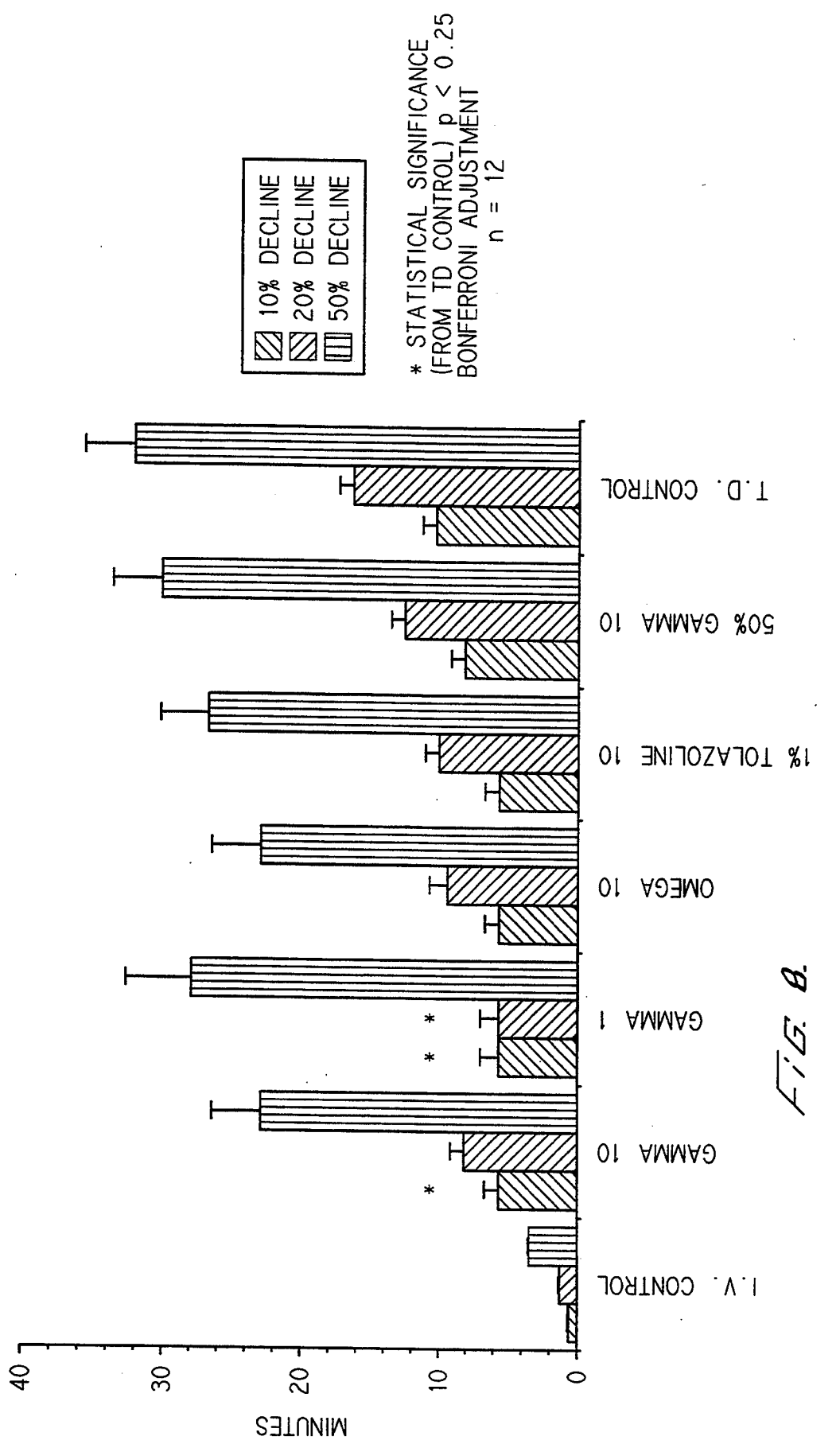
FIG. 8 is a bar graph illustrating the in vivo pharmacodynamic percent decline in heart rate for certain dermal clearance enhancer formulations.

Gamma Oil provided statistically significant dermal clearance enhancement (vs. control) in the times required to achieve both a ten and twenty percent decline in hear rate (FIG. 8). In both cases, the Gamma Oil pretreatment achieved the respective decline in heart rate nearly twice as quickly as the control. Omega® Oil experimental half-life was about fifty percent of control (18 versus 31 minutes). Although the other pretreatments were not statistically significantly different from the control, there was an observable improvement in offset over the control for all pretreatments.

TABLE VII

DERMAL CLEARANCE ENHANCER EXPERIMENTS

| CONDITION | | CHANGE IN HEART RATE (BPM) | DELAY TIME (MIN) | HALF-LIFE (MIN) | TIME TO REACH NOTED % DECLINE IN HEART RATE (MIN.) | | | | |
|---|---|---|---|---|---|---|---|---|---|
| | | | | | 10% | 20% | 30% | 40% | 50% |
| Control (BA325-01 | | 52.17 | 1.57 | 12.53 | 3.20 | 4.83 | 6.46 | 19.07 | 22.93 |
| Control (BA326-01) | | 123.25 | 1.00 | 19.89 | 6.24 | 9.16 | 12.67 | 17.19 | 21.70 |
| Control (MI309-01) | | 60.00 | 60.00 | 60.00 | 60.00 | 60.00 | 60.00 | 60.00 | 60.00 |
| Control (BA206-01) | | 88.00 | 5.50 | 60.00 | 7.07 | 98.65 | 10.21 | 16.92 | 24.25 |
| control (BO200-01) | | 56.00 | 1.50 | 60.00 | 11.00 | 60.00 | 60.00 | 60.00 | 60.00 |
| Control (PO200-01) | | 87.00 | 7.00 | 60.00 | 9.35 | 11.70 | 60.00 | 60.00 | 60.00 |
| Control (MI308-01) | | 63.00 | 5.10 | 19.23 | 8.80 | 11.70 | 14.16 | 18.71 | 24.54 |
| Control (BA233-01) | | 78.80 | 3.66 | 20.60 | 5.53 | 7.41 | 9.91 | 13.84 | 25.97 |
| Control (BO343-01 | | 54.05 | 2.28 | 13.72 | 4.53 | 6.79 | 9.23 | 11.73 | 16.68 |
| Control (BO344-01) | | 88.07 | 0.00 | 25.09 | 2.28 | 4.55 | 10.58 | 22.82 | 30.00 |
| Control (PO349-01) | | 94.17 | 1.67 | 52.48 | 9.66 | 19.65 | 29.56 | 60.00 | 60.00 |
| Control (BA328-01) | | 54.44 | 3.10 | 52.48 | 7.04 | 16.54 | 23.02 | 29.50 | 33.10 |
| Control (BB300-01) | | 58.44 | 9.20 | 13.72 | 10.79 | 23.38 | 13.98 | 16.23 | 18.58 |
| Control (BB301-01) | | 77.47 | 8.54 | 2.42 | 9.50 | 10.47 | 11.43 | 12.39 | 113.35 |
| Control (MA300-01) | | 82.88 | 1.99 | 12.81 | 4.00 | 5.04 | 8.54 | 11.49 | 15.32 |
| Control (MA301-01) | | 77.08 | 1.44 | 9.60 | 4.04 | 6.82 | 11.63 | 13.58 | 15.52 |
| Mean | | 74.68 | 7.10 | 30.91 | 10.19 | 15.98 | 21.96 | 27.72 | 31.37 |
| SEM | | 4.85 | 3.59 | 5.49 | 3.39 | 4.42 | 4.93 | 4.94 | 4.47 |
| Gamma 1 (PO350-01) | immed | 77.48 | 0.00 | 15.17 | 2.41 | 4.83 | 6.32 | 7.75 | 9.18 |
| Gamma 1 (MI312-01) | immed | 58.46 | 2.88 | 3.57 | 3.39 | 3.91 | 4.42 | 4.94 | 5.45 |
| Gamma 1 (BA330-01) | immed | 55.58 | 2.66 | 23.08 | 5.45 | 10.18 | 15.98 | 20.16 | 24.34 |
| Gamma 1 (PO351-01) | immed | 125.30 | 1.33 | 22.19 | 3.20 | 5.07 | 13.68 | 23.87 | 31.33 |
| Gamma 1 (BA331-01) | immed | 104.09 | 3.10 | 18.02 | 5.40 | 7.70 | 11.52 | 16.30 | 21.48 |
| Gamma 1 (BA332-01) | immed | 125.30 | 1.44 | 21.36 | 3.44 | 5.45 | 11.44 | 26.62 | 60.00 |
| Gamma 1 (BO345-01) | immed | 71.06 | 1.34 | 33.95 | 7.86 | 10.46 | 16.77 | 24.93 | 31.34 |
| Gamma 1 (BO34601) | immed | 95.64 | 0.00 | 27.47 | 2.48 | 4.95 | 21.01 | 31.00 | 60.00 |
| Gamma 1 (MI313-01) | immed | 93.34 | 0.78 | 19.23 | 2.15 | 3.53 | 4.90 | 14.31 | 22.35 |
| Gamma 1 (BB308-01) | immed | 60.17 | 1.44 | 10.67 | 4.15 | 5.42 | 8.53 | 10.33 | 13.00 |
| Gamma 1 (BB308-01) | immed | 90.81 | 16.08 | 15.58 | 18.33 | 20.58 | 27.97 | 35.01 | 42.05 |
| Gamma 1 (BB309-01) | immed | 95.33 | 11.64 | 14.41 | 14.50 | 19.78 | 24.97 | 28.90 | 32.82 |
| Gamma 1 (MA309-01) | immed | 76.48 | 2.22 | 7.57 | 3.43 | 4.64 | 5.85 | 7.06 | 11.27 |
| Mean | | 86.64 | 3.45 | 17.87 | 5.86 | 8.19 | 13.34 | 19.32 | 28.05 |
| SEM | | 6.41 | 1.33 | 2.26 | 1.39 | 1.59 | 2.14 | 2.76 | 4.90 |
| Gamma 10 (BO341-01) | | 74.11 | 2.40 | 11.76 | 4.22 | 6.03 | 8.10 | 10.95 | 16.09 |
| Gamma 10 (B)342-01) | | 41.13 | 2.59 | 10.47 | 4.55 | 6.50 | 9.92 | 15.62 | 21.85 |
| Garma 10 (PO346-01) | | 53.20 | 0.19 | 4.95 | 1.26 | 2.33 | 3.40 | 4.47 | 5.76 |
| Gamma 10 (PO347-01) | | 101.66 | 1.44 | 14.41 | 2.37 | 3.29 | 4.22 | 5.14 | 6.07 |
| Gamma 10 (MI305-01) | | 51.94 | 12.88 | 1.91 | 13.48 | 14.08 | 14.69 | 15.29 | 15.89 |
| Gamma 10 (BA324-01) | | 105.17 | 0.77 | 22.19 | 3.95 | 8.03 | 12.90 | 17.31 | 21.70 |
| Gamma 10 (MI310-01) | | 78.14 | 1.37 | 19.89 | 7.99 | 9.73 | 13.28 | 33.00 | 60.00 |
| Gamma 10 (BA329-01) | | 96.23 | 0.11 | 27.48 | 4.54 | 9.51 | 14.8 | 19.95 | 25.68 |
| Gamma 10 (MA306-01) | | 66.96 | 5.10 | 17.47 | 7.83 | 11.25 | 170.04 | 21.53 | 26.03 |
| Gamma 10 (MA307-01) | | 78.45 | 1.56 | 23.08 | 5.80 | 9.14 | 16.64 | 24.19 | 31.60 |
| Gamma 10 (BB30601) | | 45.33 | 1.20 | 11.76 | 3.86 | 6.53 | 8.65 | 10.83 | 12.34 |
| Gamma 10 (BB307-01) | | 89.59 | 3.99 | 14.06 | 9.52 | 12.92 | 16.17 | 19.28 | 22.39 |
| Mean | | 73.49 | 2.80 | 14.95 | 5.78 | 8.28 | 11.66 | 16.46 | 22.12 |
| SEM | | 6.38 | 1.01 | 2.16 | 0.98 | 1.037 | 1.37 | 2.33 | 4.13 |
| Delta 10 (PO413-01) | | 64.32 | 2.50 | 8.34 | 0.50 | 1.08 | 3.75 | 4.42 | 9.33 |
| Delta 10 (BO408-01) | | 71.61 | 2.88 | 13.72 | 2.00 | 3.5 | 7.58 | 12.25 | 16.17 |
| Gamma oil (MI306-01) | | 42.06 | 6.20 | 2.83 | 6.99 | 7.78 | 8.56 | 9.35 | 10.14 |
| Gamma oil (BA333-01) | | 62.21 | 5.99 | 27.57 | 7.39 | 16.85 | 23.61 | 30.37 | 36.00 |
| Gamma oil (BO347-01) | | 76.05 | 1.89 | 32.06 | 5.03 | 9.30 | 18.67 | 30.73 | 60.00 |
| Gamma oil (MI314-01) | | 61.35 | 7.65 | 23.08 | 10.90 | 14.79 | 19.07 | 22.80 | 26.51 |
| Gamma oil (PO354-01) | | 89.01 | 0.28 | 44.40 | 10.49 | 16.76 | 23.03 | 29.29 | 60.00 |
| Gamma oil (BO350-01) | | 63.16 | 3.32 | 14.41 | 5.63 | 7.93 | 11.45 | 16.25 | 22.10 |
| Gamma oil (BA336-01) | | 71.18 | 7.20 | 24.04 | 14.74 | 19.44 | 23.44 | 27.44 | 31.44 |
| Gamma oil (PO310-01) | | 99.70 | 0.00 | 13.10 | 4.49 | 7.19 | 9.66 | 12.55 | 15.52 |
| Gamma oil (MA310-01) | | 85.36 | 0.45 | 16.47 | 3.61 | 7.36 | 12.04 | 16.94 | 21.85 |
| Gamma oil (BB311-01) | | 86.53 | 8.87 | 16.47 | 11.70 | 15.15 | 20.22 | 24.38 | 28.54 |
| Gamma oil (BB311-01) | | 55.22 | 12.38 | 6.85 | 14.42 | 16.47 | 19.05 | 22.05 | 22.72 |
| Gamma oil (MA311-01 | | 45.27 | 3.78 | 13.40 | 6.26 | 8.73 | 16.55 | 19.09 | 21.63 |
| Mean | | 69.76 | 4.83 | 19.56 | 8.47 | 12.31 | 17.11 | 21.77 | 29.70 |
| SEM | | 5.21 | 1.12 | 3.30 | 1.11 | 1.33 | 1.57 | 2.04 | 4.53 |
| Omega (BA30701) | | 55.00 | 2.40 | 9.93 | 4.07 | 5.73 | 7.40 | 9.79 | 12.18 |
| Omega (BO30801) | | 57.00 | 7.00 | 17.47 | 11.75 | 14.25 | 16.63 | 23.49 | 31.19 |
| Omega (PO30901) | | 80.00 | 3.00 | 7.10 | 4.48 | 5.96 | 7.44 | 9.14 | 10.96 |
| Omega (PO31101) | | 77.00 | 3.00 | 10.29 | 4.97 | 6.95 | 8.84 | 10.63 | 12.42 |

TABLE VII-continued

DERMAL CLEARANCE ENHANCER EXPERIMENTS

| CONDITION | CHANGE IN HEART RATE (BPM) | DELAY TIME (MIN) | HALF-LIFE (MIN) | TIME TO REACH NOTED % DECLINE IN HEART RATE (MIN.) | | | | |
|---|---|---|---|---|---|---|---|---|
| | | | | 10% | 20% | 30% | 40% | 50% |
| Omega (PO31102) | 69.00 | 3.00 | 8.47 | 4.41 | 5.82 | 7.22 | 11.44 | 16.44 |
| Omega (BO31901) | 78.00 | 2.00 | 19.89 | 2.31 | 10.00 | 15.60 | 20.80 | 26.00 |
| Omega (MI31101) | 82.94 | 0.00 | 36.07 | 3.13 | 7.74 | 22.86 | 60.00 | 60.00 |
| Omega (BB304-01) | 63.56 | 11.37 | 9.29 | 13.20 | 15.03 | 18.94 | 26.09 | 32.39 |
| Omega (BB305-01) | 63.65 | 2.33 | 16.02 | 5.83 | 15.51 | 18.95 | 22.39 | 25.93 |
| Omega (MA304-01) | 56.86 | 6.87 | 7.28 | 8.37 | 9.88 | 11.38 | 20.09 | 21.22 |
| Omega (MA305-01) | 56.48 | 7.20 | 9.14 | 8.33 | 9.46 | 10.59 | 11.73 | 15.70 |
| Omega (MI327-01) | 48.79 | 5.10 | 12.53 | 6.53 | 7.96 | 9.39 | 11.15 | 13.23 |
| Omega (BA352-01) | 73.07 | 3.44 | 8.72 | 5.12 | 6.80 | 8.58 | 14.14 | 17.62 |
| Mean | 66.26 | 4.36 | 13.25 | 6.35 | 9.31 | 12.60 | 19.30 | 22.71 |
| SEM | 3.22 | 0.87 | 2.30 | 0.90 | 0.98 | 1.48 | 3.77 | 3.70 |
| 1% Tolazoline (BO300-01) | 53.00 | 2.00 | 14.06 | 7.24 | 8.85 | 10.45 | 12.29 | 19.86 |
| 1% Tolazoline (PO356-01) | 101.93 | 5.28 | 5.75 | 9.14, | 12.89 | 16.35 | 19.40 | 22.45 |
| 1% Tolazoline (PO357-01) | 80.67 | 0.67 | 10.87 | 2.56 | 4.46 | 6.18 | 7.61 | 9.04 |
| 1% Tolazoline (BA337-01) | 84.26 | 1.33 | 32.06 | 9.27 | 15.49 | 20.96 | 26.43 | 31.33 |
| 1% Tolazoline (BA338-01) | 93.54 | 1.77 | 20.60 | 4.71 | 7.55 | 10.17 | 14.58 | 21.82 |
| 1% Tolazoline (BB302-01) | 69.23 | 5.27 | 17.47 | 8.58 | 12.60 | 19.78 | 30.11 | 35.27 |
| 1% Tolazoline (BB303-01) | 92.75 | 1.81 | 12.81 | 4.56 | 10.28 | 19.70 | 28.29 | 60.00 |
| 1% Tolazoline (MI317-01) | 67.50 | 0.39 | 19.23 | 4.31 | 12.20 | 14.89 | 17.58 | 20.27 |
| 1% Tolazoline (BO352-01) | 97.31 | 0.00 | 18.60 | 2.17 | 4.12 | 7.47 | 12.20 | 19.92 |
| 1% Tolazoline (BO3051-01) | 84.22 | 0.22 | 21.36 | 4.63 | 7.66 | 11.55 | 26.06 | 66.00 |
| 1% Tolazoline (MA302-01) | 64.17 | 4.43 | 10.47 | 6.46 | 8.49 | 10.55 | 12.63 | 14.68 |
| 1% Tolazoline (MI328-01) | 87.58 | 8.02 | 18.02 | 9.64 | 11.25 | 12.87 | 16.89 | 20.44 |
| 1% Tolazoline (MI303-01) | 72.15 | 4.65 | 11.30 | 10.49 | 11.90 | 13.30 | 14.83 | 18.05 |
| Mean | 80.64 | 2.76 | 16.35 | 6.44 | 9.83 | 13.40 | 18.38 | 27.16 |
| SEM | 4.03 | 0.69 | 1.84 | 0.78 | 0.93 | 1.31 | 1.99 | 4.43 |

Example D

Transdermal Iontophoretic Delivery of Drugs in the Isolated Perfused Porcine Skin Flap Model The isolated perfused porcine skin flap (IPPSF) apparatus was developed and designed as an in vitro model to measure the absorption of agents applied to the skin by providing a means whereby the venous contents could be directly assayed. This is accomplished by isolating an island-tubed skin flap from the pig which receives its circulation from the epigastric artery and returns into the epigastric vein. A two stage surgical procedure maintains this microcirculation uncatonically correct. Pig skin is used because of its similarity in function and structure to that of man. See, Riviere et al., "The Isolated Perfused Porcine Skin Flap (IPPSF)" Fundamental and Applied Toxicology 7:444–453 (1976), the disclosure of which is incorporated herein by reference.

A temperature and humidity controlled chamber allows the isolated, tubed porcine skin flap to remain viable for up to about 12 hours. The flap is perfused via the caudal superficial epigastric artery and its paired venae commitantes with a Krebs-Ringer bicarbonate buffer (pH 7.4) containing bovine serum albumin and glucose. Viability of the flap is validated during the course of the experiment by monitoring glucose utilization and lactate production.

Skin flaps (two, one from each side of the pig) were harvested after two days using the two stage surgical procedure described by Riviere et al. Once obtained, each skin flap was connected to a nonrecirculating perfusate system in separate IPPSF plexiglass chambers by cannulation of the caudal superficial epigastric artery.

The IPPSF apparatus (as described by Riviere et al) comprises a closed, humidified chamber maintained at 37° C. Enclosed within the chamber was a nonrecirculating perfusate system whereby nutritional media for the flap was contained within reservoirs and tubing. The media is Kreb's-Ringer bicarbonate buffer at pH 7.4, containing glucose and bovine serum albumin. It was oxygenated through silastic tubing by exposure to 95% oxygen and 5% carbon dioxide and the temperature flow, pH and pressure were continually monitored during the experiment. Parameters which defined the viability of the flaps, such as glucose utilization, osmolality, arterial pH, lactate and lactate dehydrogenase production were constantly monitored.

Arbutamine was formulated (for iontophoretic delivery) at 5.3 mg/gm (about 15 mM), 7.1 mg/Gm (about 20 mM), 12.4 mg/gm (about 35 mM) and 24.7 mg/gm (about 70 mM) in an aqueous hydroxypropyl methylcellulose (HPMC) gel containing methyl and propyl parabens as preservatives, disodium EDTA as a chelating agent and sodium metabifulfite as an antioxidant (pH about 4). The indifferent electrode gel formulation was an aqueous phosphate-buffered (pH 7), HPMC gel containing parabens as preservatives and sodium chloride to adjust conductivity.

The Gensia electrodes (manufactured by Graphic Control, Inc. Buffalo, N.Y.), used in the majority of experiments were reservoir-type with a 14 mm diameter×5 mm deep well to contain about one gram of the arbutamine or Indifferent gels. The reservoir was contained in a 58 mm ×45 mm oval adhesive-coated polyethylene foam which has a silver/silver chloride backing. The cross-sectional area of the gel reservoir was 1.54 cm$^2$.

The Trans Q[1] electrode (manufactured by IOMED, Inc. Salt Lake City, Utah) was used in the IPPSF model to increase the area of drug administration. The hydrated gel matrix makes the TransQ[1] electrode area approximately equal to 7 cm$^2$. It consists of a gel matrix which is approximately 1.6 mm wide×4.5 mm long. The gel is hydrated with 1.5 mls of drug solution immediately prior to use and is attached to an adhesive backing.

Current for iontophoretic delivery of arbutamine was supplied by a Life-Tech Iontophore (Life-Tech, Inc., Houston, Tex.) Model 6110A. This was a battery powered device which adjusts a driving voltage to maintain a constant current to the electrode Ag/AgCl backing. This current subsequently drives the positively charged arbutamine molecules into the skin.

Current was applied to the electrodes via lead wires from the Life-Tech Iontophor. Following current delivery the electrodes were removed and any gel remaining at the surface was gently removed.

The arbutamine-containing and Indifferent electrodes were adhered to the IPPSF via the electrode adhesive. The potential "dose" or $I*T*C*A$ of arbutamine delivered is a product of the percent Drug Concentration (%)×Current ($mA/cm^2$)×Duration of Current (minutes)×Area of Electrode ($cm^2$).

The standard protocol for dermal clearance enhancers (DCE) administration was a 10 minutes pretreatment interval prior to arbutamine iontophoretic delivery. Tolazoline, gamma oil, Rubriment Oil ® and Omega Oil ® are examples of DCEs studied in the skin flap. All the pretreatments, except Tolazoline, were oils or ointments which were carefully rubbed into the skin for a few seconds. Tolazoline was iontophoretically delivered.

From 1.5 to 2.5 milliliter samples are collected from the venous effluent of the IPPSF and adjusted to pH 5-6 using 1N HCl. Aliquots (0.4 ml) of each sample were then filtered using an Amicon Ultrafree Micropartition device using a Beckman Model T-J6 bench top centrifuge at 2000 ×g for 30 minutes.

Fifty microliters of the filtrate were injected into a reversed phase high performance liquid chromatography system for analysis of arbutamine. The HPLC system consisted of a Whatman Partisphere C18 reversed phase column, 4.6×110 mm, 5 micron. The analysis was run under isocratic conditions at room temperature using a mobile phase consisting of 40% v/v methanol, 2%v/v glacial acetic acid, 5 mM heptanesulfonic acid, 58% v/v water. The pH of the mobile phase was not adjusted. Ultraviolet detection was at 280 nm.

This HPLC method determined the free arbutamine in the media and did not extract the drug which was bound to the bovine albumin in the IPPSF perfusate media. Therefore, drug concentrations analyzed for the IPPSF samples, using this HPLC method, were corrected for 64% protein binding of the arbutamine to the albumin to obtain corrected free drug values.

Tolazoline and components of gamma oil such as capsaicin and methyl nicotinate were assayed to determine whether DCEs entered the microcirculation during pretreatment.

Figure 9A:
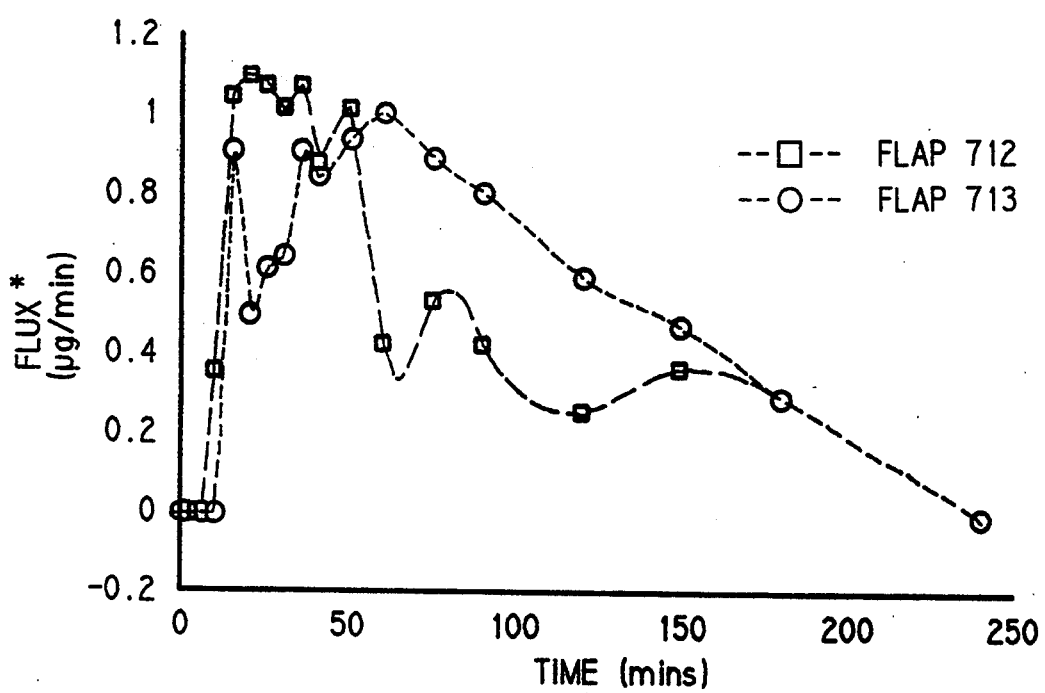
FIGS. 9A and 9B are plots of arbutamine flux versus time for two different skin flaps.

Initially, each skin flap was profiled for assayed drug concentration, flux cumulative amount, flow, pressure, vascular resistance and impedance with respect to time. Using the arbutamine concentration values, flux (micrograms/minute) was calculated as the product of concentration (micrograms/milliliter) and flow (milliliters/minute) for each sampling time. Because flux is directly proportional to area, and the area of the electrode remains constant, area was not used in the flux calculation in the skin flaps. A typical flux versus time plot is shown in FIG. 9A for skin flaps 712 and 713 which were done using a 35 mM arbutamine electrode with current density of 1.0 $mA/cm^2$ for 10 minutes.

Figure 9B:
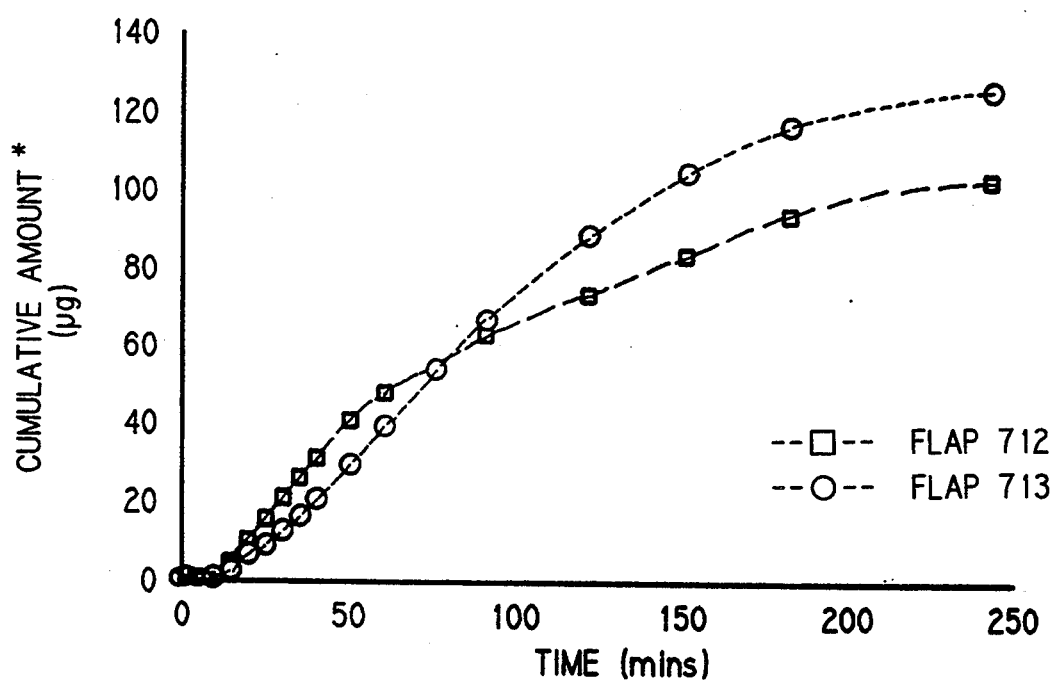

Cumulative amount (micrograms) or area under the curve (AUC) values were determined by the integration of the flux curve with respect to time. Cumulative amount versus time is shown in FIG. 9B for flaps 712 and 713.

The parameters of primary importance when comparing flaps with differing $I*T*C$ values are the peak flux, cumulative amount and simulated peak plasma concentration.

Figure 10A:
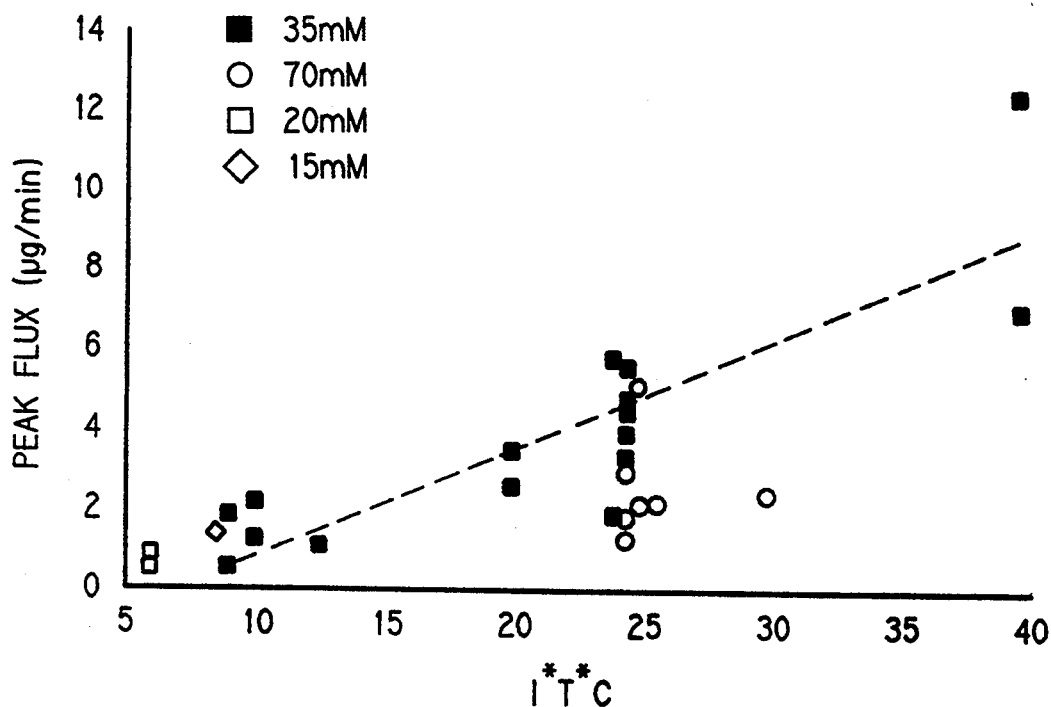
FIGS. 10A and 10B depict plots of peak flux versus I*T*C and simulated peak plasma concentration versus I*T*C respectively.

The $I*T*C$ is a predictor of flux can be used to compare the dose of arbutamine across all experimental groups. A plot of the peak flux versus $I,T*C$ for all flaps (without dermal clearance enhancers) is shown in FIG. 10A. There is very good linear correlation (R=0.87) for the 35 mM flaps. There appears to be a trend for the 70 mM flaps to exhibit lower peak fluxes than flaps using 35 mM arbutamine concentrations. For an $I*T*C$ of approximately 25 mA-min-% Concentration/$cm^2$, the mean peak flux for 35 mM flaps was approximately 4 $\mu$g/min whereas the mean peak flux for the 70 mM flaps was around 2.5 $\mu$g/min. Arbutamine is said to effect alpha adrenergic receptors, therefore the 70 mM arbutamine concentration may sufficiently increase vasoconstriction which subsequently produced lower arbutamine peak flux than the 35 mM concentration.

Figure 10B:
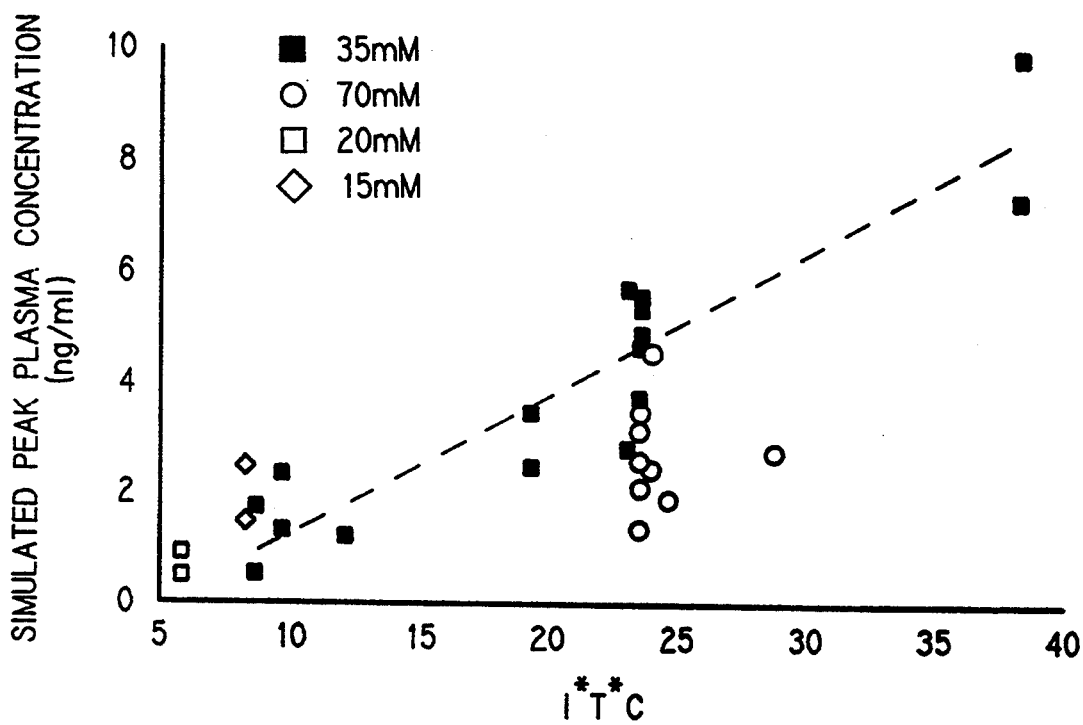

In FIG. 10B, simulated peak plasma concentration was plotted versus $I*T*C$. Again, the 70 mM flaps showed lower (e.g., as expected in man) predicted values of arbutamine plasma levels than the 35 mM flaps because of the lower flux. In addition, 35 mM skin flaps completed using an $I*T*C$ of approximately 25, predict peak arbutamine plasma concentrations of around 4 ng/ml. This IPPSF estimation of 4 ng/ml was within range of the arbutamine plasma levels shown in human clinical studies to be needed to adequately increase the heart rate for evaluation of the heart during exercise stress testing.

Figure 11A:
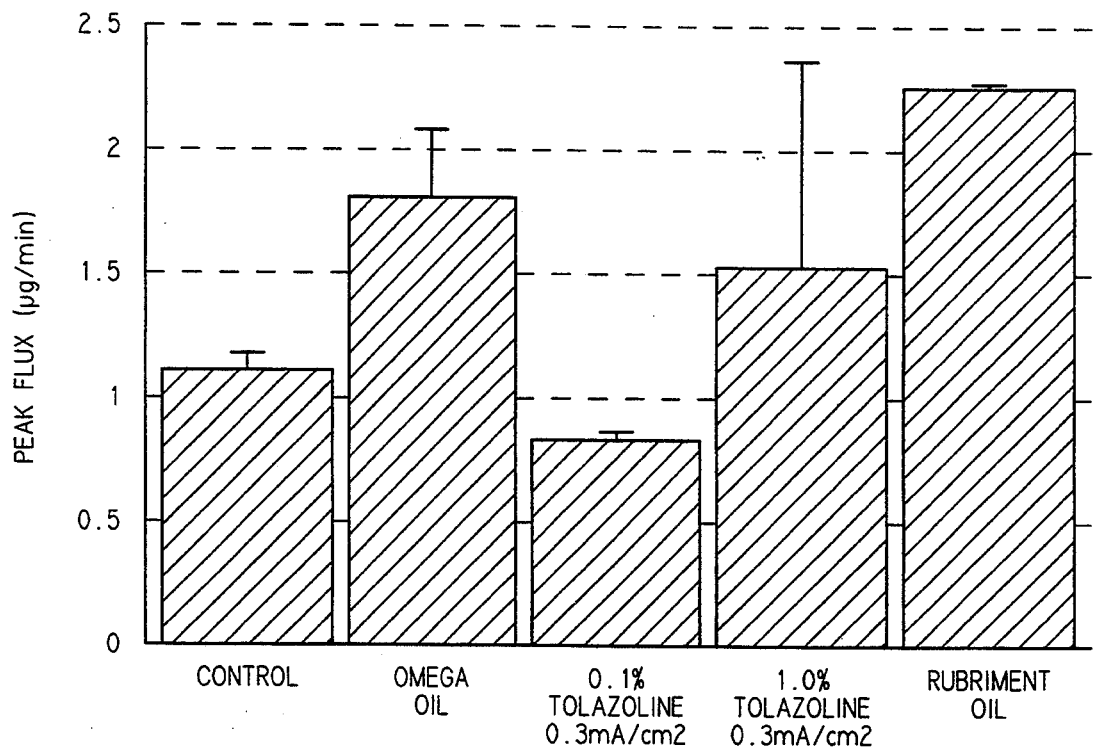
FIGS. 11A, 11B and 11C are plots of peak flux (11A), cumulative amount (11B) and simulated peak plasma concentrations of arbutamine for different DCE pretreatment formulations as compared to control for isolated perfused porcine skin flap (IPPSF).
Figure 11B:
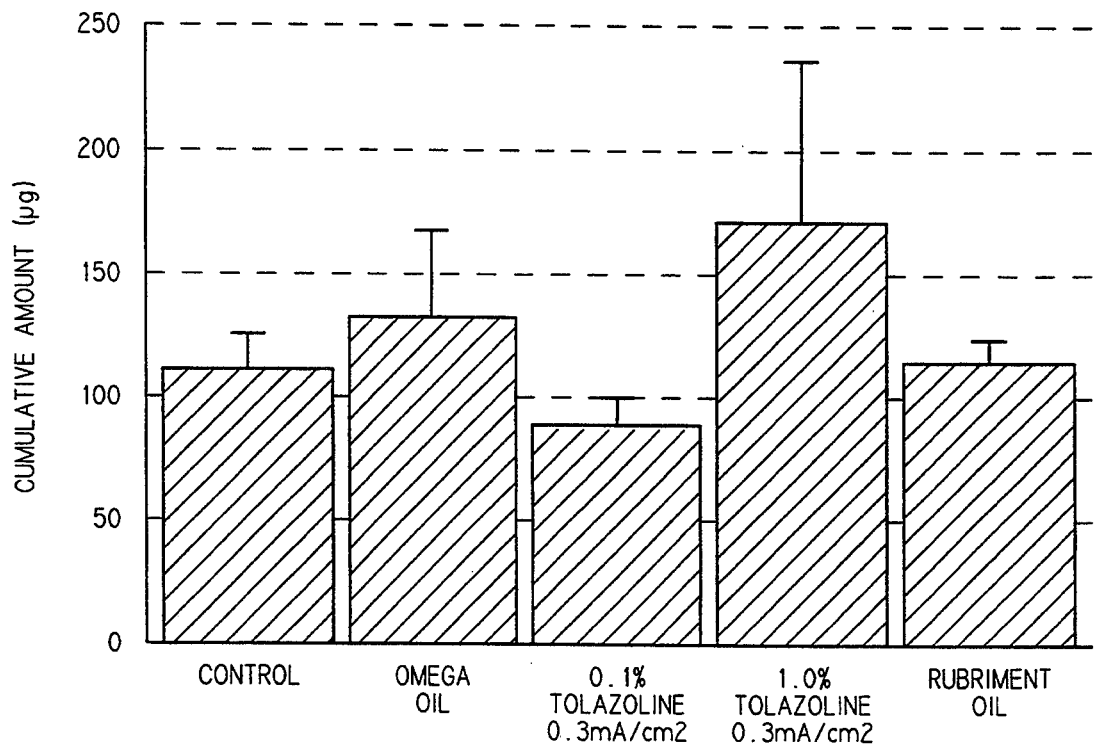
Figure 11C:
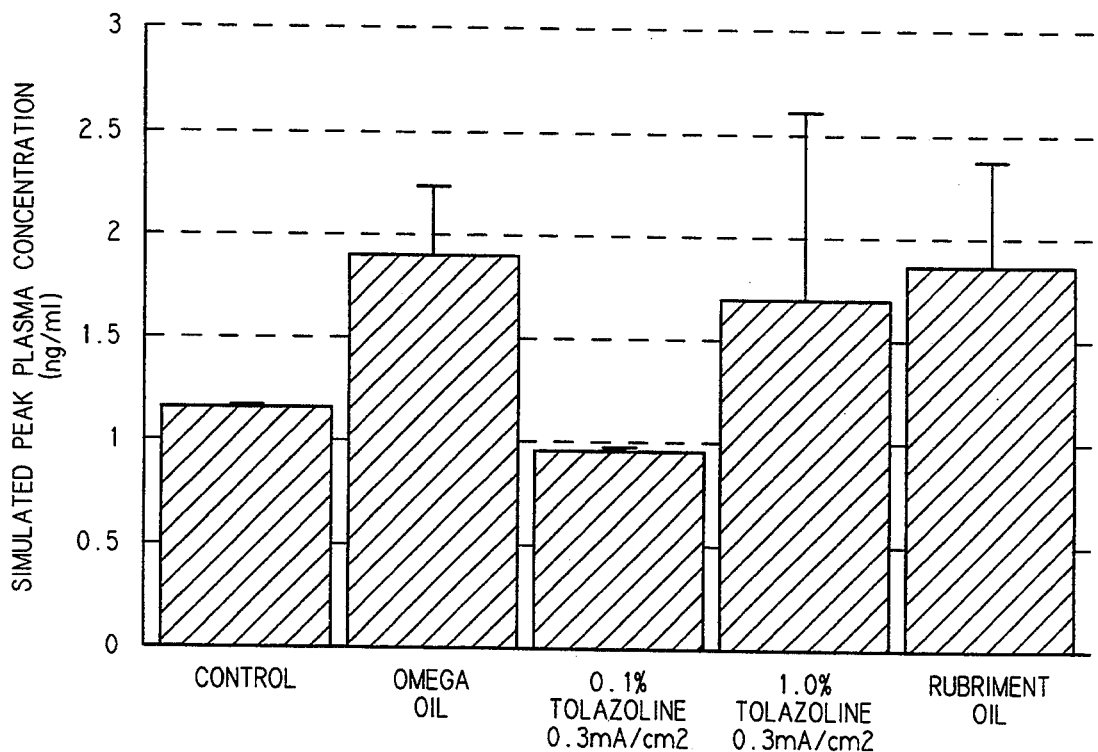

Using the IPPSF, various DCEs can be compared with each other to determine what effects they have on arbutamine peak flux and cumulative amount as well as simulated peak plasma concentration. FIGS. 11A to C represent a series of IPPSF experiments which was done using a 35 mM arbutamine electrode delivered at a current density of 1.0 $mA/cm^2$ for 10 minutes. Control flaps had no pretreatment. Four sets of flaps were pretreated for 10 minutes with one of four DCEs. The DCEs used were either Omega Oil ®, 0.1% Tolazoline, 10% Tolazoline or Rubriment Oil ®.

FIGS. 11A, 11B and 11C depict plots of the control and how it compared to the four DCE agents with respect to peak flux, cumulative amount and simulated peak plasma concentration, respectively. The skin flaps pretreated with Rubriment Oil ® showed higher peak flux than control arbutamine peak flux and simulated peak plasma concentration, yet gave the same cumulative amount as control. Omega Oil ® and 1.0% Tolazoline also showed higher than control values for peak flux, cumulative amount and simulated peak plasma concentration.

Figure 12A:
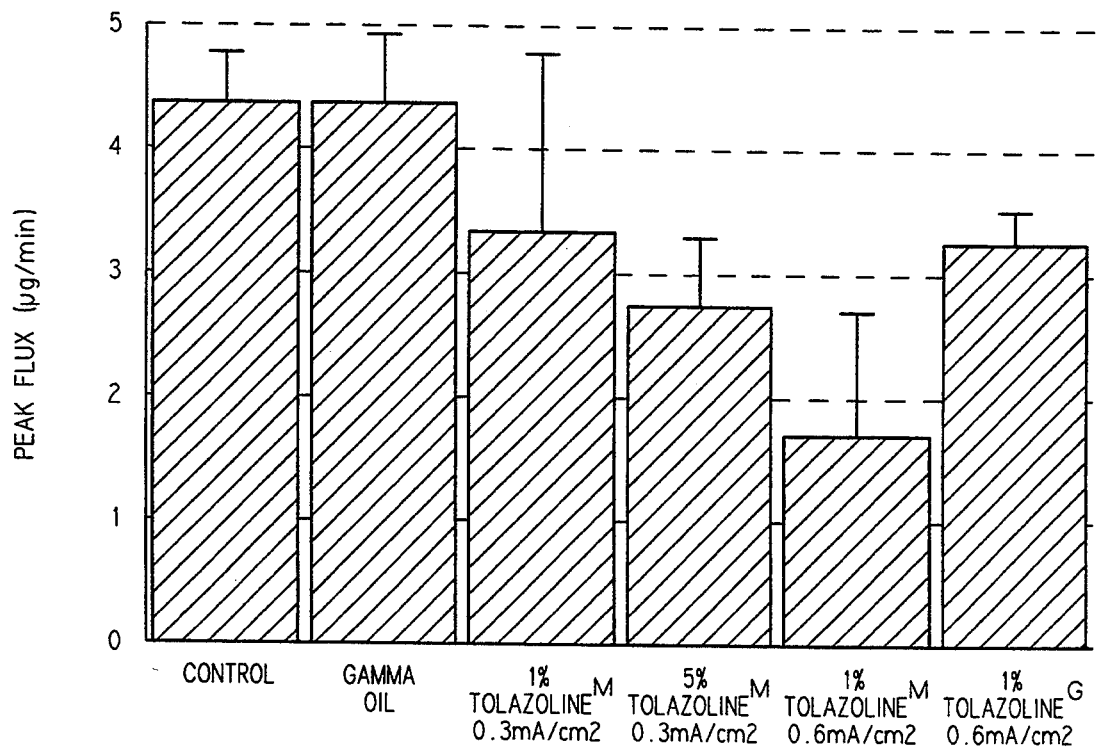
FIGS. 12A, 12B and 12C are plots of peak flux (12A), cumulative amount (12B) and simulated peak plasma concentration (12C) of arbutamine for different DCE formulations as compared to control.
Figure 12B:
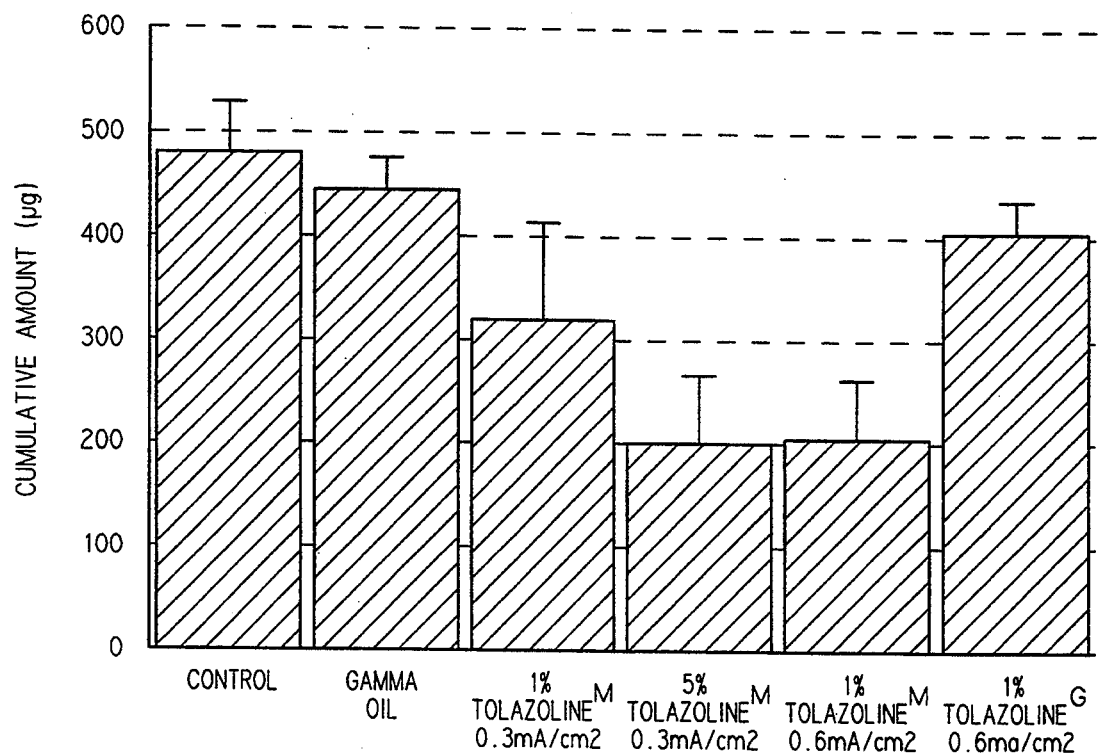
Figure 12C:
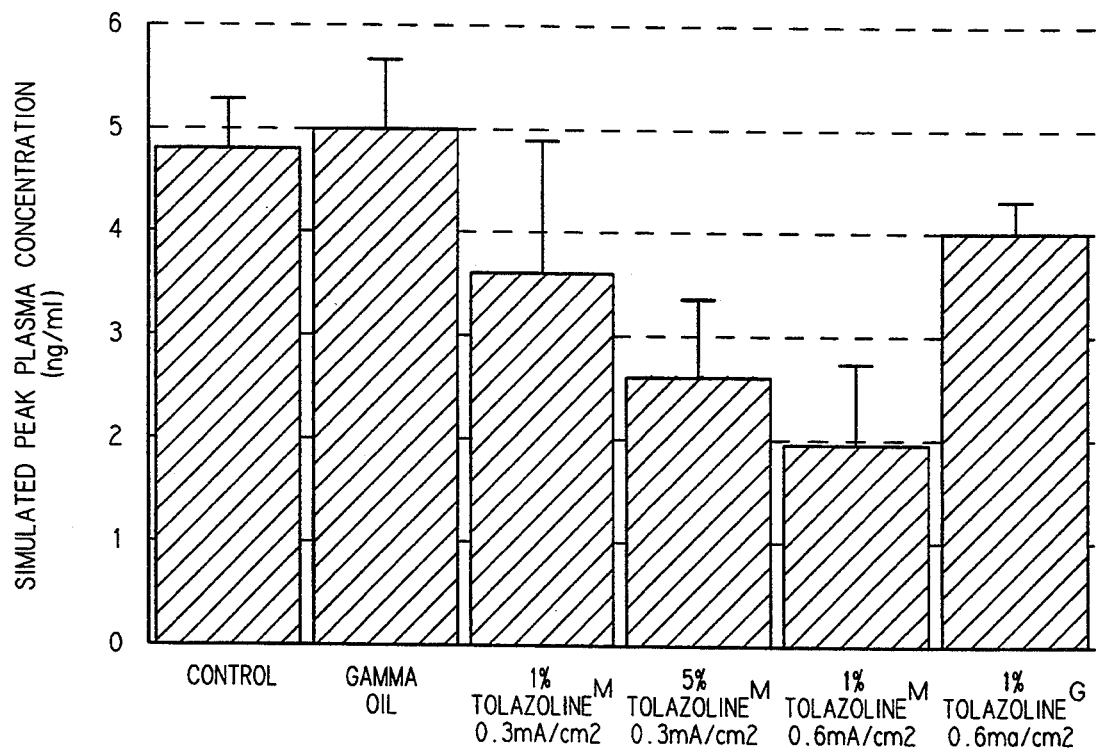

FIGS. 12A to C represent plots of control and five different DCE pretreatments with respect to arbutamine peak flux, cumulative amount and simulated peak plasma concentration. Gamma oil and Tolazoline were investigated in this series of flaps as the two 10 minutes DCEs prior to the delivery of 35 mM arbutamine at 0.7 $mA/cm^2$ for 28 minutes. Parameters for the iontophoretic delivery of Tolazoline were varied to determine whether Tolazoline delivery could be optimized to increase arbutamine peak plasma and amount. Tolazoline is an α-blocker and may inhibit vasoconstriction in the microcirculation from vasoconstricting upon iontophoretic delivery of arbutamine. In this series of experiments, Tolazoline did not appear to promote the parameters of interest for arbutamine as depicted in FIGS. 12A to C. Gamma oil compared equally to control for the peak flux, cumulative amount, and simulated peak plasma concentration.

FIGS. 12A to C also compared the iontophoretic delivery of Tolazoline using the Life-Tech (Life-Tech, Inc., Houston, Tex.) Meditrode gauze electrode versus the Graphic Control electrode (same electrode used to deliver arbutamine). The Meditrode electrode used Tolazoline solution whereas the Graphic Control electrode incorporated Tolazoline gel. The Graphic Control electrode promoted a two fold increase in the peak flux, cumulative amount and simulated peak plasma concentration of arbutamine over the Meditrode electrode.

A group of IPPSF experiments were done using a 70 mM arbutamine electrode, iontophoretically delivered at a 0.7 mA/cm$^2$ current density for 14 minutes. Half of the flaps were pretreated for 10 minutes with gamma oil and half had no pretreatment (control). Gamma oil increased the arbutamiune peak flux, cumulative amount and simulated peak plasma concentration versus control (see FIGS. 13A to C).

Figure 14A:
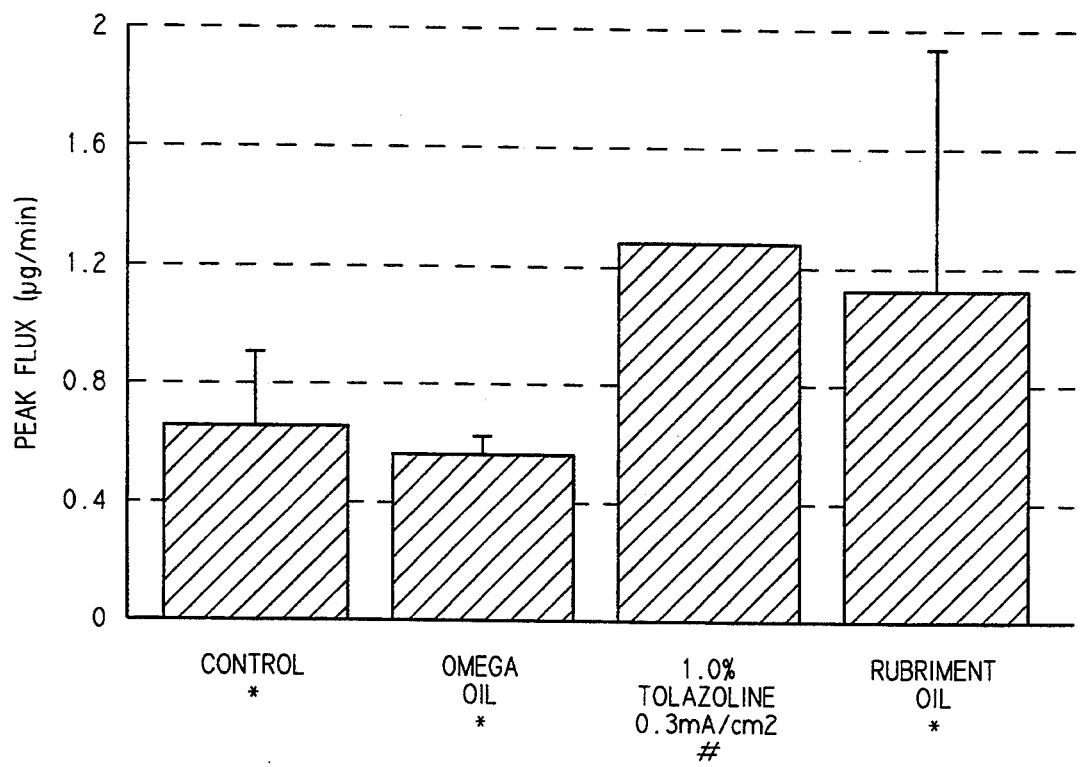
FIGS. 14A, 14B and 14C are plots of peak flux (14A), cumulative amount (14B) and simulated peak plasma concentration (14C) for different pretreatments with DCE formulations as compared to control.
Figure 14B:
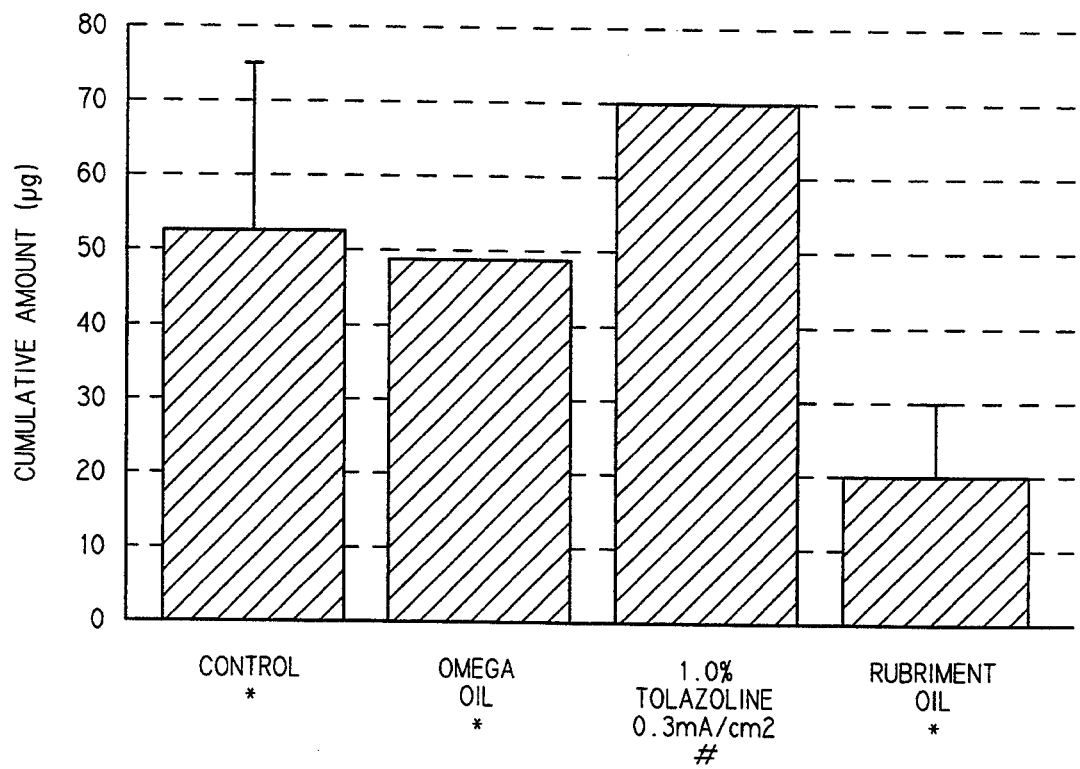
Figure 14C:
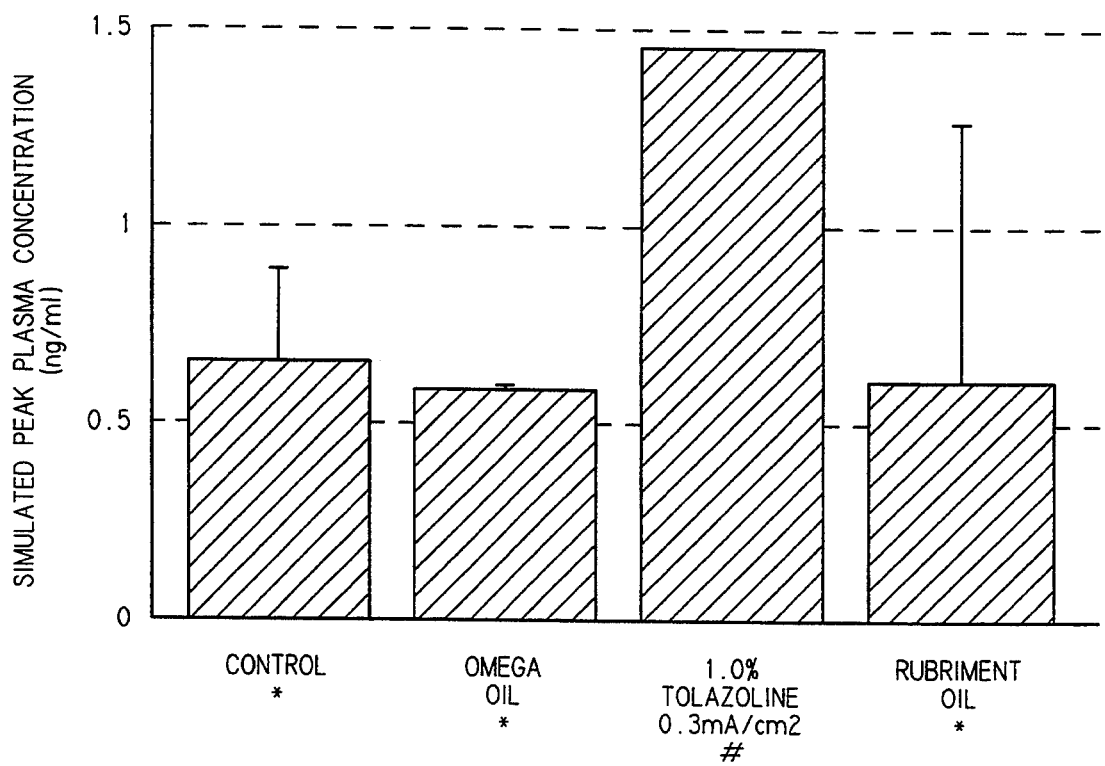

Control compared to three different DCE pretreatments was done using a 20 mM arbutamine electrode iontophoretically delivered at 0.6 mA/cm$^2$ current density for 14 minutes (FIGS. 14A to C). The 10 minute pretreatment of 1.0% Tolazoline delivered at 0.3 mA/cm$^2$ promoted a two fold increase in peak arbutamine flux and simulated peak plasma concentration, as well as a 50% increase in arbutamine cumulative amount. Rubriment Oil ® increased peak flux of arbutamine by 66% over control, but did not improve arbutamine cumulative amount or simulated peak plasma concentration compared to control. Omega Oil ® did not enhance arbutamine flux, amount or simulated plasma concentration over control in this situation.

Figure 13A:
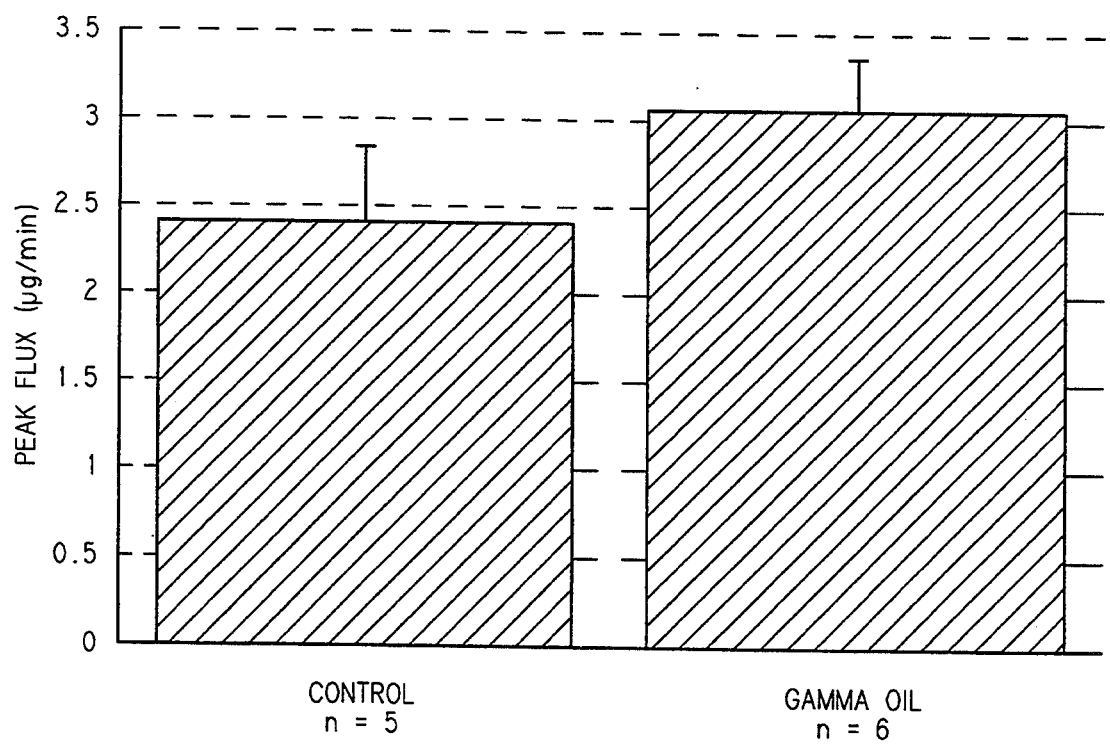
FIGS. 13A, 13B and 13C are plots of peak flux (13A), cumulative amount (13B), and simulated peak plasma concentration of arbutamine for pretreatment with one of the topical formulations of the present invention compared with control.
Figure 13B:
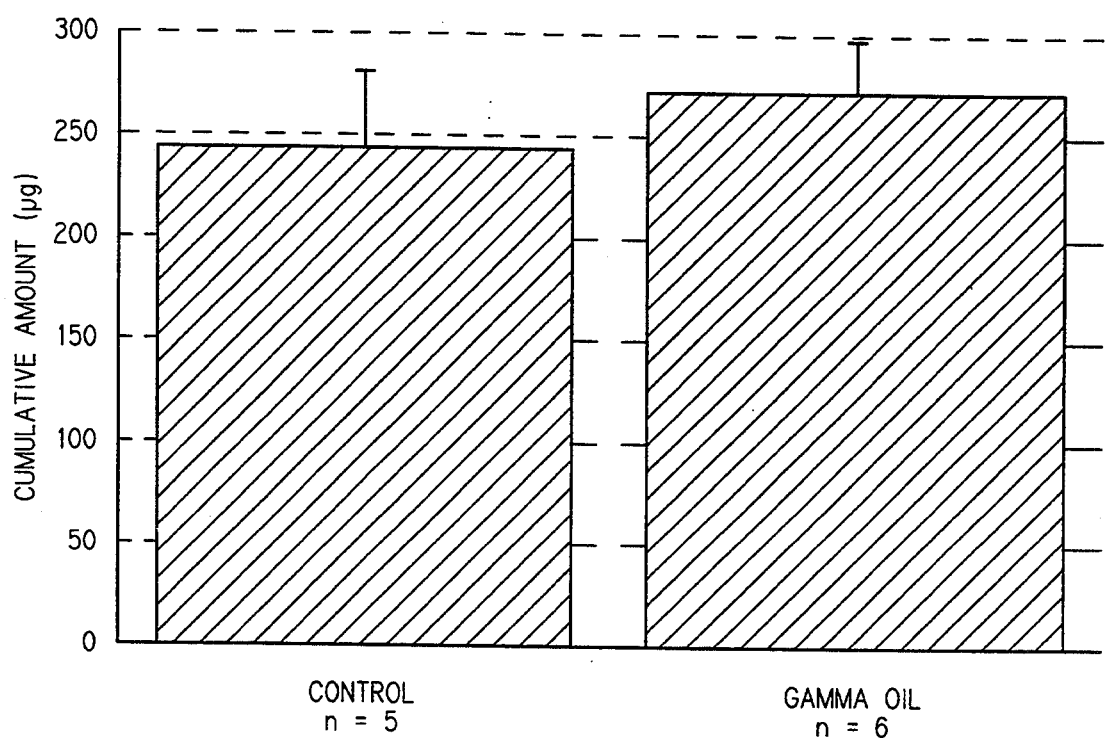
Figure 13C:
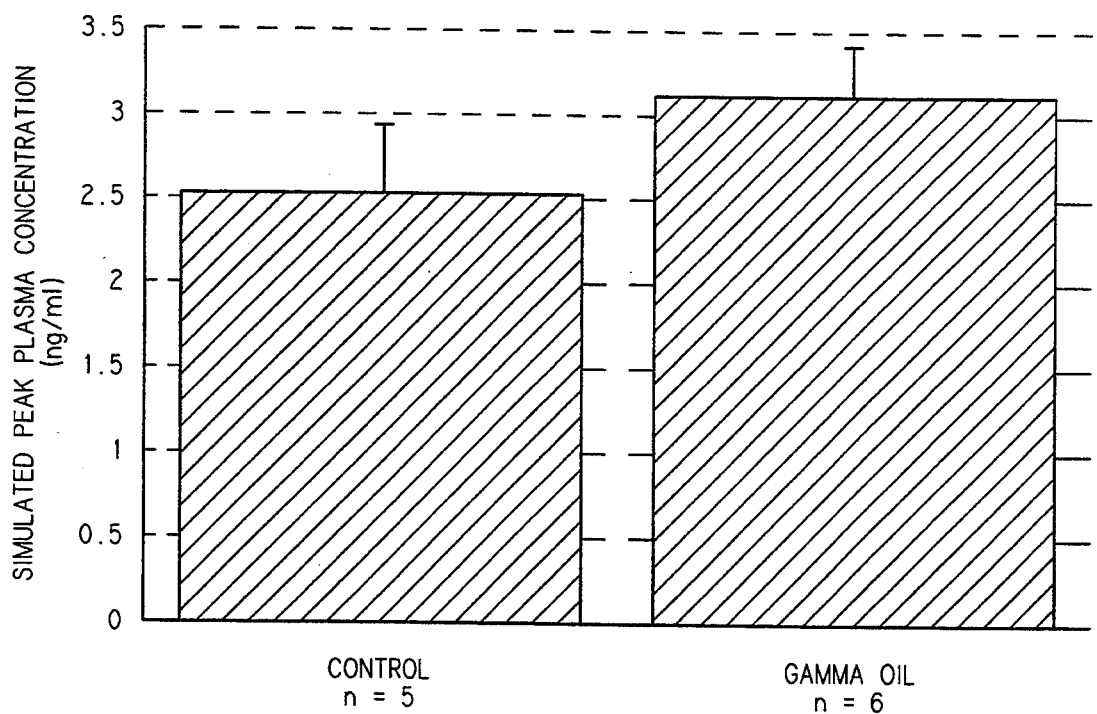

As observed in FIGS. 13A to C, at an I*T*C of 24.24, gamma oil appeared to enhance the parameters of peak flux and cumulative amount and when used with the 70 mM electrode. In FIGS. 12A to C, the dermal clearance enhancers did not appear to enhance the parameters versus control for the 35mM electrode at the identical I*T*C. However, when the I*T*C was lowered (12.37) using the 35 mM electrode, dermal clearance enhancers again augmented the values of the parameters (FIGS. 11A to C).

Subsequently, a group of skin flap experiments was completed with the 35 mM electrode at the lower I*T*C (12–14) but area was now increased 4.5 times by using the TransQ$^1$ electrode (7 cm$^2$) in place of the Gensia electrode (1.54 cm$^2$) in order to achieve a total dose (I*T*C*A) that would be sufficient to achieve desired plasma levels. The TransQ$^1$ electrode (flaps 1080/1081 and 1108/1109), did not adversely effect the peak flux, cumulative amount and simulated peak plasma levels versus control.

1% Tolazoline appeared to be a beneficial DCE at the lower I*T*C values of 5.94 and 12.24% Conc-mA-min/cm$^2$ for 20 mM and 35 mM arbutamine electrode concentrations, respectively. Rubriment Oil ® also promoted arbutamine peak flux, cumulative amount and simulated peak plasma concentration at I*T*C of 12.24 using the 35 mM arbutamine electrode. Gamma Oil appeared to be a good DCE when used in conjunction with the 70 mM arbutamine electrode concentration at the higher I*T*C of 24.24% Conc-mA-min/cm$^2$.

Increasing the area of the Arbutamine electrode appeared to benefit the delivery of the drug and is currently being pursued in greater detail.

The IPPSF has been used as a model to predict arbutamine concentrations over time and the effects of DCE agents in man. There has been good correlation between arbutamine release rate profiles predicted by the IPPSF and profiles seen in man during human clinical studies for a given I*T*C*A.

BIBLIOGRAPHY

1. Barry, B., *Dermatological Formulations, Percutaneous Absorption*, Marcell Dekker, Inc., New York (1983), p. 36.
2. Federal Register, Vol. 48, No. 27, page 5868, Tuesday, Feb. 8, 1983.
3. Federal Register, Vol. 44, No. 234, pages 69804–05, Tuesday, Dec. 4, 1979.
4. *The United States Pharmacopeia*, Twenty-First Revision, official from Jan. 1, 1985. *The National Formulary*, Sixteenth Edition, official from Jan. 1, 1985, United States Pharmacopeia Convention, Inc., pages 72–73.
5. A. Leung, *Encyclopedia of Common Natural Ingredients Used in Food, Drugs and Cosmetics*, John Wiley & Sons, pages 86–87.
6. Tregear, A., *Physical Functions of Skin*, Academic Press, London and New York (1966), p. 14.
7. Norman, A., J. Theor. Biol., *Diffusional Spread of Iontophoretically Injected Ions*, 52, 159–162 (1975).
8. Tojo, K., et al,, Stratum Corneum Reservoir Capacity Affecting Dynamics of Transdermal Drug Delivery, Drug Dev. Ind. Pharm., (4) , 561–572 (1988) .
9. Drill, *Pharmacology in Medicine*, 4th Ed. (1971), p. 1035.
10. Goodman and Gillman, *The Pharmacologic Basis Therapeutic*, 6th Ed. (1980), p. 955.
11. Riviere, J., et al., *Transdermal Lidocaine Iontophoresis in Isolated Perfused Porcine Skin*, presented at the Percutaneous Absorption Section, The Sixth Symposium on Cutaneous Toxicity, American Academy of Dermatology, Washington, D.C. (Sept., 1988).
12. *Martindale The Extra Pharmacopoeia*, Twenty-eighth Edition. Edited by J. Reynolds, The Pharmaceutical Press, 1982, reprinted with corrections in May, 1984, pages 672, 1626 and 1629.
13. Guy, A. H., et al., *Rapid Radial Transport of Methyl Nicotinate in the Dermis*, Arch. Dermatol. Res. 273, pp. 91–95 (1982).
14. Tur, E., et al., *Noninvasive Assessment of Local Nicotinate Pharmacodynamics by Photoplethymography*, Jour. Inves. Dermatol. 80, pp. 499–503 (1933).
15. Collins, A. P., et al., *Some Observations on the Pharmacology of "Deep-Heat" a Topical Rubifacient*, Ann. Rheumatic Diseases, 43, pp. 411–415 (1984).

We claim:

1. An improved method of iontophoretic administration of a drug to a subject comprising the steps of:
   selecting a site on the subject's skin for iontophoretic administration of the drug;
   administering a formulation capable of increasing blood flow to the subject's skin near the site and prior to iontophoretic administration of the drug;

allowing sufficient time to pass for the formulation to effect increased flow of blood in the skin near the site on the subject's skin; and iontophoretically administering the drug to the subject at the site; wherein said formulation includes from about 0.1 to about 5% methyl nicotinate and from about 0.02% to about 0.3% capsaicin in a vehicle of which comprises a short chain aliphatic alcohol, light mineral oil or propylene glycol and methyl salicylate, in a ratio which comprises about 2 to about 6 parts alcohol and about 1 to about 4 parts mineral oil or propylene glycol per part methyl salicylate.

2. A method according to claim 1 wherein said vehicle comprises 2.9 parts ethyl alcohol and 2.0 parts propylene glycol per part methyl salicylate.

3. The method according to claim 2 wherein said formulation comprises about 0.27% (w/w) methyl nicotinate and about 0.028% capsaicin.

4. A method according to claim 1 wherein said vehicle comprises 2.9 parts isopropyl alcohol and 2.0 parts mineral oil per part methyl salicylate.

5. The method according to claim 4 wherein said formulation comprises 0.27% (w/w) methyl nicotinate and 0.028% capsaicin.

6. An improved method of iontophoretic administration of a drug to a subject comprising the steps of:

selecting a site on the subject's skin for iontophoretic administration of the drug;

administering a formulation capable of increasing blood flow to the subject's skin near the site and prior to iontophoretic administration of the drug;

allowing sufficient time to pass for the formulation to effect increased flow of blood in the skin near the side on the subject's skin; and iontophoretically administering the drug to the subject at the site;

wherein said formulation contains methyl salicylate, 17.5%; histamine dihydrochloride, 0.02%; methyl ester of nicotinic acid, 0.27%; and capsicum oleoresin, 0.24% in an isopropyl alcohol and water vehicle.

7. An improved method of iontophoretic administration of a drug to a subject comprising the steps of:

selecting a site on the subject's skin for iontophoretic administration of the drug;

administering a formulation capable of increasing blood flow to the subject's skin near the site and prior to iontophoretic administration of the drug;

allowing sufficient time to pass for the formulation to effect increased flow of blood in the skin near the side on the subject's skin; and iontophoretically administering the drug to the subject at the site;

wherein said formulation contains methyl salicylate, 15%; capsaicin, 0.025%; and camphor, 3.6% in 70% alcohol with acetone.

8. An improved method of iontophoretic administration of a drug to a subject comprising the steps of:

selecting a site on the subject's skin for iontophoretic administration of the drug;

administering a formulation capable of increasing blood flow to the subject's skin near the site and prior to iontophoretic administration of the drug;

allowing sufficient time to pass for the formulation to effect increased flow of blood in the skin near the side on the subject's skin; and iontophoretically administering the drug to the subject at the site;

wherein said formulation includes 0.24% capsaicin and 0.27% methyl nicotinate by weight.

* * * * *

UNITED STATES PATENT AND TRADEMARK OFFICE
CERTIFICATE OF CORRECTION

PATENT NO. : 5,383,848
DATED : January 24, 1995
INVENTOR(S) : HILLMAN, Robert S. et al.

It is certified that error appears in the above-identified patent and that said Letters Patent is hereby corrected as shown below:

```
Column 27, Line 40, TABLE VII:

[Gamma 1 (BO34601)     immed should read--
 Gamma 1 (BO346-01)    immed
```

Signed and Sealed this

Thirtieth Day of May, 1995

Attest:

BRUCE LEHMAN

*Attesting Officer*    *Commissioner of Patents and Trademarks*